(12) United States Patent
Susan et al.

(10) Patent No.: US 8,338,411 B2
(45) Date of Patent: Dec. 25, 2012

(54) COMPOUNDS

(75) Inventors: Edit Susan, Dunakeszi (HU); Kinga Boer, Pomaz (HU); Zoltan Kapui, Budapest (HU); Geza Timari, Vecses (HU); Sandor Batori, Budapest (HU); Zoltan Szlavik, Budapest (HU); Endre Mikus, Budapest (HU); Judit Vargane Szeredi, Budapest (HU); Michel Finet, Le Vesinet (HU); Katalin Urban Szabo, Budapest (HU); Tibor Szabo, Budapest (HU)

(73) Assignee: Sanofi, Paris (FR)

( * ) Notice: Subject to any disclaimer, the term of this patent is extended or adjusted under 35 U.S.C. 154(b) by 143 days.

(21) Appl. No.: 12/631,139

(22) Filed: Dec. 4, 2009

(65) Prior Publication Data
US 2010/0216786 A1   Aug. 26, 2010

Related U.S. Application Data

(63) Continuation of application No. PCT/HU2008/000063, filed on Jun. 2, 2008.

(30) Foreign Application Priority Data

Jun. 7, 2007   (HU) .................................... 0700395

(51) Int. Cl.
*A61K 31/535* (2006.01)
*C07D 215/38* (2006.01)

(52) U.S. Cl. ................ 514/233.2; 514/253.03; 514/293; 546/159; 546/82; 544/126; 544/361

(58) Field of Classification Search ............... 514/233.2, 514/253.03, 293; 544/126, 361; 546/159, 546/82
See application file for complete search history.

(56) References Cited

U.S. PATENT DOCUMENTS

| 7,176,213 B2 * | 2/2007 | Aranyi et al. | 514/292 |
| 7,365,089 B2 * | 4/2008 | Aranyi et al. | 514/383 |
| 2005/0124648 A1 * | 6/2005 | Aranyi et al. | 514/292 |

FOREIGN PATENT DOCUMENTS

| DE | 2551879 | 5/1976 |
| WO | 02/081474 A1 | 10/2002 |
| WO | 03/010167 A1 | 2/2003 |
| WO | 03/053973 A1 | 7/2003 |
| WO | WO 03/053968 | 7/2003 |

OTHER PUBLICATIONS

K. T. Potts, et al., "1, 2, 4-Triazoles, XIII, Derivatives of the s-Triazolo[1,5-α]pyridine Ring System", *J. Org. Chem.*, 1966, 31(1), pp. 260-265.
G. Hajos, et al., "A New Synthesis of the s-triazolo[1,5-α]pyridine Ring System", *Monatshefte für Chemic.*, 1995, 126, pp. 1213-1216.
C. N.Hoang, et al., "A Convenient synthesis of 2-substituted [1,2,4]triazolo-[1,5-α]quinolines and [1,2,4]triazolo[5,1-α]isoquinolines", *ARKIVOC*, 2001, (ii), pp. 42-50.
Hungarian Search Report dated Nov. 14, 2007 issued in counterpart Hungarian Priority Application No. P0700395.

* cited by examiner

*Primary Examiner* — Rei-tsang Shiao
(74) *Attorney, Agent, or Firm* — Serena Farquharson-Torres; Scully, Scott, Murphy & Presser, P.C.

(57) ABSTRACT

The present invention relates to the adenosine $A_3$ receptor ligands of the general formula (I),

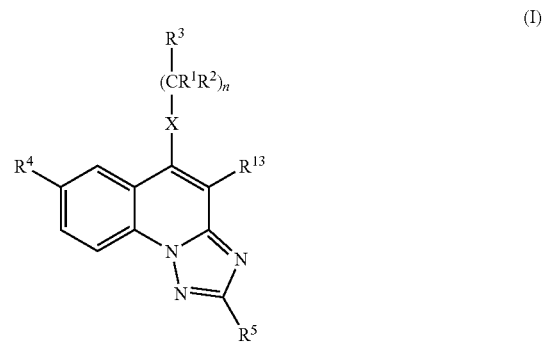

within them favourably to the antagonists, to their salts, solvates, N-oxides and isomers, to the pharmaceutical compositions containing the compounds of the general formula (I), their salts, solvates, N-oxides and isomers, to the use of the compounds of the general formula (I), their salts, solvates, N-oxides and isomers, to the preparation of the compounds of the general formula (I), their salts, solvates, N-oxides and isomers, as well as to the new intermediates of the general formula (II), (VI), (XI), (XII) and (XV), and to the preparation thereof.

15 Claims, No Drawings

COMPOUNDS

The present invention relates to the adenosine $A_3$ receptor ligands of the general formula (I), within them favourably to the antagonists, to their salts, solvates, N-oxides and isomers, to the pharmaceutical compositions containing the compounds of the general formula (I), their salts, solvates, N-oxides and isomers, to the use of the compounds of the general formula (I), their salts, solvates, N-oxides and isomers, to the preparation of the compounds of the general formula (I), their salts, solvates, N-oxides and isomers, as well as to the new intermediates of the general formula (II), (VI), (XI), (XII) and (XV), and to the preparation thereof.

Adenosine is a well-known component of several biologically active endogenous molecules (ATP, $NAD^+$, nucleic acids). Besides, it plays an important regulatory role in many physiological processes. The effect of adenosine on heart function was discovered already in 1929. (Drury and Szent-györgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for inhibiting the adenylate cyclase by coupling to $G_i$ membrane protein, partly influences other second messenger systems. The $A_2$ receptor subtype can be subdivided into two further subtypes—$A_{2a}$ and $A_{2b}$—, which receptors stimulate the adenylate cyclase activity. The sequence of adenosine $A_3$ receptors have been recently identified from rat testis cDNA library. Later it was proved that it corresponds to a novel, functional adenosine receptor. The activation of the $A_3$ receptors is connected also with several second-messenger systems, as for instance inhibition of adenylate cyclase and stimulation of phospholipase C and D.

The adenosine receptors are found in several organs and regulate their functions. Both $A_1$ and $A_{2a}$ receptors play important roles in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors, which located relatively in a higher amount in the striatum, display a functional interaction with dopamine receptors in regulating the synaptic transmission. The $A_{2a}$ adenosine receptors on endothelial and smooth muscle cells are responsible for adenosine-induced vasodilation (Baraldi P G et al. Chem. Rev. 2008, 108, 238-263).

On the basis of mRNA identification, the $A_{2b}$ adenosine receptors are widely distributed in different tissues. They have been identified almost in every cell type, but its expression is the highest in the intestine and the bladder. This subtype probably also has important regulatory function in the regulation of the smooth muscle tone of the blood vessel and plays a role in the function of mast cells (Volpini R et al. Curr. Topics in Med. Chem. 2003, 3, 427-443).

Expression levels for $A_3$ adenosine receptors are rather low comparing to other subtypes and highly species dependent. $A_3$ adenosine receptors are expressed primarily in the central nervous system, testis, and immune system and appear to be involved in the modulation of mediator release from mast cells in immediate hypersensitivity reaction and in neutrophilic granulocyte migration (Y. Chen et al., Science 2006, 314:1792-1795).

For therapeutic use it is essential to ensure that the molecules are selective towards other adenosine receptors therefore does not bind, or bind only in the case of very high concentration to the $A_1$, $A_{2a}$ and $A_{2b}$ sub-types of the adenosine receptor.

The $A_3$ antagonists published so far in the literature belong to the groups of flavonoides, 1,4-dihydropyridine derivatives, thiazolonaphthyridines, thiazolopyrimidines and aminoquinolines. However, many of the effective and to the adenosine subtypes selective antagonists are of strongly lipophilic character, consequently, they have poor aqueous solubility. This property hinders their in vivo application. As it is seen in the literature, the number of studies directed to the preparation of water soluble adenosine A3 receptor antagonists, is increasing (Ch. E. Müller et al., J. Med. Chem. 45:3440, 2002; A. Maconi et al., J. Med. Chem. 45:3579, 2002).

Patent application WO 03/053968 describes triazoloquinoline derivatives, a novel structural group of effective adenosine $A_3$ antagonists. The compounds of the general formulae (1) and (1a) of patent application WO 03/053968 are adenosine $A_3$ antagonists with high selectivity.

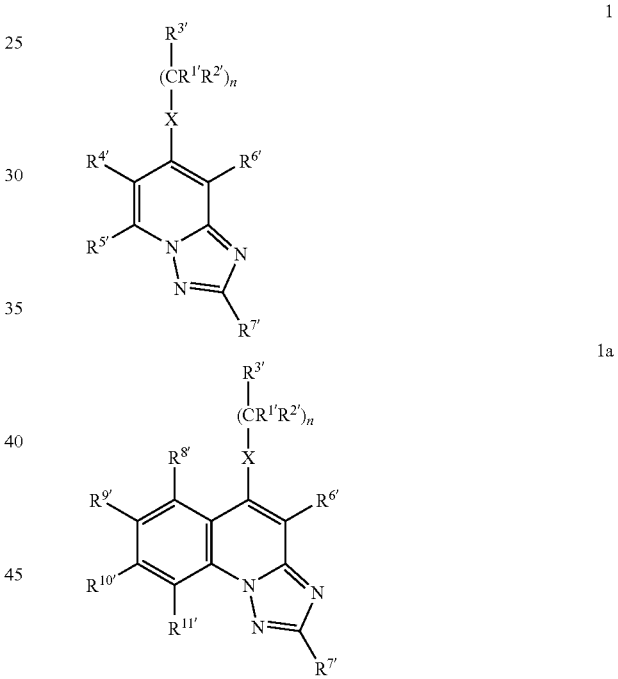

Patent application of publication number WO 03/053968 claims compounds of the general formulae (1) and (1a), wherein $R^{1'}$ stands for hydrogen atom or a straight or branched $C_{1-4}$ alkyl group;

$R^{2'}$ stands for hydrogen atom or a straight or branched $C_{1-4}$ alkyl group;

$R^{3'}$ stands for hydrogen atom or a straight or branched $C_{1-4}$ alkyl group, or a phenyl group, thienyl group, or furyl group, optionally substituted by one or more straight or branched $C_{1-4}$ alkyl group, straight or branched $C_{1-4}$ alkoxy group, or halogen atom, or for a 5- or 6 membered heteroaromatic ring—containing one, two or three nitrogen atoms or one nitrogen atom and one oxygen atom or one nitrogen atom and one sulphur atom—optionally substituted by one or more straight or branched $C_{1-4}$ alkyl group, straight or branched $C_{1-4}$ alkoxy group, or halogen atom;

$R^{6'}$ stands for hydrogen atom or a cyano group, aminocarbonyl group, $C_{1-4}$ alkoxycarbonyl group, or carboxyl group;

$R^{7'}$ stands for hydrogen atom or a straight or branched $C_{1-4}$ alkyl group, or a phenyl, benzyl, thienyl, furyl group, optionally substituted by a methylenedioxy group, or one or more straight or branched $C_{1-4}$ alkyl group, straight or branched $C_{1-4}$ alkoxy group, hydroxyl group, trifluoromethyl group, cyano group or halogen atom, or for a 5 or 6 membered heteroaromatic ring—containing one, two or three nitrogen atoms or one nitrogen atom and one oxygen atom or one nitrogen atom and one sulphur atom—optionally substituted by one or more straight or branched $C_{1-4}$ alkyl group, straight or branched $C_{1-4}$ alkoxy group, or halogen atom, $R^{8'}$, $R^{9'}$, $R^{10'}$, and $R^{11'}$ independently mean hydrogen atom, straight or branched $C_{1-4}$ alkyl group, straight or branched $C_{1-4}$ alkoxy group, hydroxyl group or halogen atom; or $R^{8'}$ and $R^{11'}$ stand for hydrogen atom and $R^{9'}$ and $R^{10'}$ together form a methylenedioxy group;

X stands for a —$CH_2$— group, —NH— group, —$NR^{8'}$— group, or a sulphur atom or an oxygen atom or a sulfo group or a sulfoxy group wherein $R^{8'}$ stands for a straight or branched $C_{1-4}$ alkyl group or $C_{3-6}$ cycloalkyl group;

n has a value of zero, 1 or 2— and their salts, solvates and optically active isomers and the salts, solvates thereof.

These compounds, too, have the characteristic disadvantage that they dissolve in water very poorly, sometimes not at all, what renders their drugability difficult.

We aimed to prepare new adenosine $A_3$ ligands with quinoline skeleton, within them favourably antagonists, which have strong antagonistic effect and are selective to the $A_3$ receptor, i.e. they inhibit the $A_3$ receptor in much smaller concentration as compared to the $A_1$, $A_{2a}$ and $A_{2b}$ receptors. We also aimed that the stability, bioavailability, metabolism, therapeutic index, toxicity and solubility of the new compounds allow their development into a drug substance. A further aim was that the compounds, due to their favourable enteric absorption, can be administered orally.

We have found that the compounds of the general formula (I),

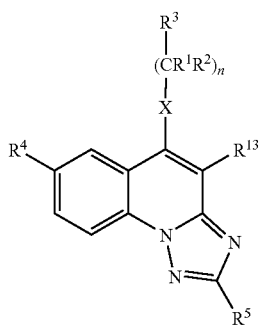

(I)

wherein $R^1$ stands for hydrogen atom or for straight or branched $C_{1-4}$ alkyl group;

$R^2$ stands for hydrogen atom or for straight or branched $C_{1-4}$ alkyl group;

$R^3$ stands for hydrogen atom or for straight or branched $C_{1-4}$ alkyl group, or $C_{3-6}$ cycloalkyl group, or a phenyl- or thienyl-, or furyl group, optionally substituted with one or more, identical or different, straight or branched $C_{1-4}$ alkyl group, straight or branched $C_{1-4}$ alkoxy group, hydroxyl group or halogen atom, or a 5- or 6-membered heterocyclic ring containing one or two or three nitrogen atoms, or a 5-membered heterocyclic ring containing one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, hydroxyl group or halogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a),

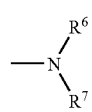

(a)

wherein $R^6$ and $R^7$ independently stand for hydrogen atom, $C_{3-6}$ cycloalkyl group or benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b),

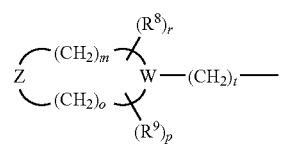

(b)

wherein $R^8$ and $R^9$ independently stand for straight or branched $C_{1-4}$ alkyl group, $C_{3-6}$ cycloalkyl group or hydroxyl group;

Z means oxygen atom, sulphur atom, —$CHR^{11}$— group or —$NR^{12}$— group—where $R^{11}$ and $R^{12}$ independently stand for hydrogen atom, straight or branched $C_{1-4}$ alkyl group, $C_{3-6}$ cycloalkyl group, benzyl group, or —$CH_2$—($C_{1-5}$ straight or branched acyl)group, —$CH_2$—$CH_2$—O—($C_{1-4}$ straight or branched alkyl)-group or $C_{1-5}$ straight or branched acyl group;

W means nitrogen atom or —CH— group;

m is a value of 1, 2 or 3;

o is a value of 1, 2 or 3;

p is a value of zero or 1;

r is a value of zero or 1;

t is a value of zero or 1;

$R^5$ stands for hydrogen atom, straight or branched $C_{1-4}$ alkyl group, or
- a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
- a 5- or 6-membered heterocyclic ring containing one or two or three or four nitrogen atoms, or one nitrogen atom and one oxygen atom, or one nitrogen atom and one sulphur atom, optionally substituted with one or more identical or different straight or branched $C_{1-4}$ alkyl group, straight or branched $C_{1-4}$ alkoxy group, hydroxyl group or halogen atom;

$R^{13}$ stands for cyano group, aminocarbonyl group, —CO—O—($C_{1-4}$ straight or branched alkyl) group or carboxyl group;

X means —$CH_2$— group, —NH— group, —$NR^{10}$— group, or sulphur atom, or oxygen atom, or —SO— or —$SO_2$— group—where $R^{10}$ stands for straight or branched $C_{1-4}$ alkyl group or $C_{3-6}$ cycloalkyl group;

n is a value of zero, 1 or 2;

and their salts, solvates, N-oxides and isomers, as well as the salts and solvates thereof, fulfil the above criteria, they have better solubility than the known triazolo-3-cyanoquinoline derivatives, and at the same time, they retain the strong adenosine A3 antagonistic effect and the selectivity.

Furthermore, we have found that the compounds of the general formula (I) according to the invention exhibit outstanding anti-inflammatory effect.

A further advantage of the compounds of the general formula (I) is that they have very favourable metabolism properties. The triazole ring is stable, during its metabolism the undesired aromatic amines are not formed.

Another advantage of the compounds of the general formula (I) according to the present invention is that they have favourable pharmacokinetic properties.

Detailed meanings of the above substituents are as follows:

By halogen atom we mean chloro-, fluoro-, iodo- or bromo atom.

By a straight or branched $C_{1-4}$ alkyl group we mean methyl-, ethyl-, propyl-, isopropyl-, butyl-, isobutyl-, secondary-butyl-, tertiary-butyl-, preferably ethyl- or methyl group.

By a straight or branched $C_{1-4}$ alkoxy group we mean methoxy-, ethoxy-, propoxy-, isopropoxy-, butoxy-, isobutoxy-, secondary-butoxy-, tertiary-butoxy-, preferably ethoxy- or methoxy group.

By a $C_{3-6}$ cycloalkyl group we mean cyclopropyl-, cyclobutyl-, cyclopentyl- or cyclohexyl group.

By a $C_{1-5}$ acyl group we mean formyl-, acetyl, propionyl-, 2-methyl-propionyl, butyryl- or valeryl group.

By a 5- or 6-membered heterocyclic ring containing one, two, three or four nitrogen atoms we mean an aromatic ring or an unsaturated, partly saturated or fully saturated heterocyclic ring, e.g. pyrrole, imidazole, pyrazole, 1,2,3-triazole, 1,2,4-triazole, tertazole, pyridine, pyrimidine, pyridazine, pyrazine, 1,2,4-triazine, 1,3,5-triazine 1,2,4,5-tetrazine, pyrroline, imidazoline, pyrazoline ring. The ring is optionally substituted with $C_{1-4}$ alkyl-, or alkoxy group or hydroxyl group or with halogen atom.

The heterocycle containing one nitrogen atom and one oxygen atom or one nitrogen atom and one sulphur atom may be an aromatic ring, unsaturated, partially saturated or saturated heterocycle, for example oxazole, isoxazole, thiazole, isothiazole, 1,2-oxazine, 1,3-oxazine, 1,4-oxazine, 1,2-tiazine, 1,3-tiazine, 1,4-tiazine ring. The ring is optionally substituted with $C_{1-4}$ alkyl or alkoxy group or hydroxyl group or with halogen atom.

Group (b) is preferably pyrrolidino, piperidino, piperazino, 4-methylpiperazino, 4-acetylpiperazino, 4-acetylmethylpiperazino, 4-ethoxyethylpiperazino, 4-benzylpiperazino, morpholino or 2,6-dimethylmorpholino group.

By salts of the compounds of the general formula (I) we mean salts given with inorganic and organic acids. Preferred salts are those given with pharmaceutically accepted acids as for instance hydrochloric acid, sulphuric acid, ethanesulfonic acid, tartaric acid, malic acid, citric acid, fumaric acid. The salts formed during purification or isolation e.g. methanesulfonates and tetrafluoroborates are also subject of the invention.

By solvates we mean solvates given with various solvents, as for instance with water, methyl-ethyl-ketone or ethanol.

The nitrogen atoms in the triazolo-quinoline ring or optionally in the substituents $R^3$, $R^4$ or $R^5$ may be oxidized to N-oxides.

By isomers we mean structural or stereoisomers. The structural isomers may be tautomers being in equilibrium or they may be isolated desmotrops, which are also subjects of the invention. The compounds of the general formula (I) may contain one or more asymmetric carbon atoms (e.g. depending on the meanings of $R^1$, $R^2$, and $R^3$), thus, they can exist in the form of optical isomers, enantiomers or diastereoisomers. These enantiomers and diastereoisomers, as well as their mixtures, including the racemates, are also subjects of the invention.

A narrower group of the compounds of the general formula (I) is formed by the those, wherein $R^1$ stands for hydrogen atom or for straight or branched $C_{1-4}$ alkyl group;

$R^2$ stands for hydrogen atom or for straight or branched $C_{1-4}$ alkyl group;

$R^3$ stands for hydrogen atom or for straight or branched $C_{1-4}$ alkyl group, or $C_{3-6}$ cycloalkyl group, or
- a phenyl- or thienyl-, or furyl group, optionally substituted with one or more, identical or different, straight or branched $C_{1-4}$ alkyl group, straight or branched $C_{1-4}$ alkoxy group, or halogen atom, or
- a 5- or 6-membered heterocyclic ring containing one or two or three nitrogen atoms, or
- a 5-membered heterocyclic ring containing one nitrogen atom and one oxygen atom, or
- one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
- a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or
- a group of the general formula (a), wherein
  $R^6$ and $R^7$ independently stands for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein
$R^8$ and $R^9$ independently stand for straight or branched $C_{1-4}$ alkyl group or $C_{3-6}$ cycloalkyl group;
Z means oxygen atom, sulphur atom, —$CHR^{11}$— group or —$NR^{12}$— group—where $R^{11}$ and $R^{12}$ independently stand for hydrogen atom, straight or branched $C_{1-4}$ alkyl group, $C_{3-6}$ cycloalkyl group, benzyl group, or —$CH_2$—($C_{1-5}$ straight or branched acyl)— group, —$CH_2$—$CH_2$—O—($C_{1-4}$ straight or branched alkyl)— group or $C_{1-5}$ straight or branched acyl group;
W means nitrogen atom or —CH— group;
m is a value of 1, 2 or 3;
o is a value of 1, 2 or 3;
p is a value of zero or 1;
r is a value of zero or 1;
t is a value of zero or 1;
$R^5$ stands for hydrogen atom, straight or branched $C_{1-4}$ alkyl group, or
a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;
$R^{13}$ stands for cyano group, aminocarbonyl group, —CO—O—($C_{1-4}$ straight or branched alkyl) group or carboxyl group;
X means —$CH_2$— group, —NH— group, —$NR^{10}$— group, or sulphur atom, or oxygen atom, or —SO— or —$SO_2$— group—where $R^{10}$ stands for straight or branched $C_{1-4}$ alkyl group or $C_{3-6}$ cycloalkyl group;
n is a value of zero, 1 or 2;
and their salts, solvates, N-oxides and isomers, as well as the salts and solvates thereof.

A further narrower group of the compounds of the general formula (I) is formed by those
wherein
$R^1$ stands for hydrogen atom or for straight or branched $C_{1-4}$ alkyl group;
$R^2$ stands for hydrogen atom or for straight or branched $C_{1-4}$ alkyl group;
$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or
a 5- or 6-membered heterocyclic ring containing three nitrogen atoms, or a 5-membered heterocyclic ring containing one nitrogen atom and one oxygen atom or one nitrogen atom and one sulphur atom optionally substituted with straight or branched $C_{1-4}$ alkyl group, straight or branched $C_{1-4}$ alkoxy group or halogen atom;
$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or
a group of the general formula (a), wherein
$R^6$ and $R^7$ independently stand for hydrogen atom, $C_{3-6}$ cycloalkyl group or benzyl group, or
a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or
a group of the general formula (b), wherein
$R^8$ and $R^9$ independently stand for straight or branched $C_{1-4}$ alkyl group or $C_{3-6}$ cycloalkyl group;
Z means oxygen atom, sulphur atom, —$CHR^{11}$— group or —$NR^{12}$— group—where $R^{11}$ and $R^{12}$ independently stand for hydrogen atom, straight or branched $C_{1-4}$ alkyl group, $C_{3-6}$ cycloalkyl group, benzyl group, or —$CH_2$—($C_{1-5}$ straight or branched acyl)— group, —$CH_2$—$CH_2$—O—($C_{1-4}$ straight or branched alkyl)— group or $C_{1-5}$ straight or branched acyl group;
W means nitrogen atom or —CH— group;
m is a value of 1, 2 or 3;
o is a value of 1, 2 or 3;
p is a value of zero or 1;
r is a value of zero or 1;
t is a value of zero or 1;
$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;
$R^{13}$ stands for cyano group;
X means —NH— group;
n is a value of zero, 1 or 2;
and their salts, solvates and isomers and the salts and solvates thereof.

Another narrower group of the compounds of the general formula (I) is formed by those,
wherein
$R^1$ stands for hydrogen atom or for methyl group;
$R^2$ stands for hydrogen atom or for methyl group;
$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or
a 5- or 6-membered heterocyclic ring containing one or two or three nitrogen atoms, or
a 5-membered heterocyclic ring containing one nitrogen atom and one oxygen atom or one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a 6-membered heterocyclic ring containing one nitrogen or a group of the general formula (a), wherein
$R^6$ and $R^7$ independently stands for a straight or branched $C_{1-4}$ alkyl group—, or a group of the general formula (b), wherein
$R^8$ and $R^9$ independently stand for straight or branched $C_{1-4}$ alkyl group;

Z means oxygen atom, or $—NR^{12}—$ group—where $R^{12}$ stands for hydrogen atom, straight or branched $C_{1-4}$ alkyl group, benzyl group or acetyl group;

W means nitrogen atom;
m is a value of 2;
o is a value of 2;
p is a value of zero or 1;
r is a value of zero or 1;
t is a value of zero;

$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group;
X means —NH— group;
n is a value of zero, 1 or 2;
and their salts, solvates N-oxides and isomers and the salts and solvates thereof.

Another narrower group of the compounds of the general formula (I) is formed by those,
wherein
$R^1$ stands for hydrogen atom or for methyl group;
$R^2$ stands for hydrogen atom or for methyl group;
$R^3$ stands for a phenyl group, or
6-membered heterocyclic ring containing one nitrogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a), wherein
$R^6$ and $R^7$ independently stands for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein
$R^8$ and $R^9$ independently stand for straight or branched $C_{1-4}$ alkyl group or $C_{3-6}$ cycloalkyl group;

Z means oxygen atom, sulphur atom, $—CHR^{11}—$ group or $—NR^{12}—$ group—where $R^{11}$ and $R^{12}$ independently stand for hydrogen atom, straight or branched $C_{1-4}$ alkyl group, $C_{3-6}$ cycloalkyl group, benzyl group, or $—CH_2—(C_{1-5}$ straight or branched acyl)-group, $—CH_2—CH_2—O—(C_{1-4}$ straight or branched alkyl)-group or $C_{1-5}$ straight or branched acyl group;

W means nitrogen atom or —CH— group;
m is a value of 1, 2 or 3;
o is a value of 1, 2 or 3;
p is a value of zero or 1;
r is a value of zero or 1;
t is a value of zero or 1;

$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group;
X means —NH— group;
n is a value of zero, 1 or 2;
and their salts, solvates, N-oxides and isomers and the salts and solvates thereof.

Another narrower group of the compounds of the general formula (I) is formed by those,
wherein
$R^1$ stands for hydrogen atom or for methyl group;
$R^2$ stands for hydrogen atom or for methyl group;
$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or a 5- or 6-membered heterocyclic ring containing one or two or three nitrogen atoms, or a 5-membered heterocyclic ring containing one nitrogen atom and one oxygen atom or one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a), wherein
$R^6$ and $R^7$ independently stands for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein
$R^8$ and $R^9$ independently stand for straight or branched $C_{1-4}$ alkyl group or $C_{3-6}$ cycloalkyl group;
Z means oxygen atom, sulphur atom, —$CHR^{11}$-group or —$NR^{12}$— group—where $R^{11}$ and $R^{12}$ independently stand for hydrogen atom, straight or branched $C_{1-4}$ alkyl group, $C_{3-6}$ cycloalkyl group, benzyl group, or —$CH_2$—$(C_{1-5}$ straight or branched acyl)-group, —$CH_2$—$CH_2$—O—$(C_{1-4}$ straight or branched alkyl)-group or $C_{1-5}$ straight or branched acyl group;
W means nitrogen atom or —CH— group;
m is a value of 1, 2 or 3;
o is a value of 1, 2 or 3;
p is a value of zero or 1;
r is a value of zero or 1;
t is a value of zero or 1;

$R^5$ stands for a phenyl group, optionally substituted with methoxy group, hydroxyl group, or halogen atom, or
a 5- or 6-membered heterocyclic ring containing one nitrogen atom, or one nitrogen atom and one sulphur atom;
$R^{13}$ stands for cyano group;
X means —NH— group;
n is a value of zero, 1 or 2;
and their salts, solvates, N-oxides and isomers and the salts and solvates thereof.

A further narrow group of the compounds of the general formula (I) is formed by those,
wherein
$R^1$ stands for hydrogen atom or methyl group;
$R^2$ stands for hydrogen atom or methyl group;
$R^3$ stands for a phenyl- or thienyl-, or furyl group, or
a 5- or 6-membered heterocyclic ring containing one or two or three nitrogen atoms, or
a 5-membered heterocyclic ring containing one nitrogen atom and one oxygen atom or one nitrogen atom and one sulphur atom;
$R^4$ stands for a 5- or 6-membered heterocyclic ring containing one or two or three or four nitrogen atoms, or one nitrogen atom and one oxygen atom, or one nitrogen atom and one sulphur atom, or
a group of the general formula (a), wherein
$R^6$ and $R^7$ independently stands for hydrogen atom, $C_{3-6}$ cycloalkyl group, benzyl group, or a straight or branched $C_{1-4}$ alkyl group-, or
a group of the general formula (b), wherein
$R^8$ and $R^9$ independently stand for straight or branched $C_{1-4}$ alkyl group;
Z means oxygen atom, or —$NR^{12}$— group—where $R^{12}$ stands for hydrogen atom, straight or branched $C_{1-4}$ alkyl group, $C_{3-6}$ cycloalkyl group, benzyl group, or —$CH_2$-acetyl group, —$CH_2$—$CH_2$—O—$CH_2$—$CH_3$ group or acetyl group;
W means nitrogen atom or —CH— group;
m is a value of 2;
o is a value of 2;
p is a value of zero or 1;
r is a value of zero or 1;
t is a value of zero;

$R^5$ stands for a phenyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
a 5- or 6-membered heterocyclic ring containing one or two or three or four nitrogen atoms, or one nitrogen atom and one oxygen atom, or one nitrogen atom and one sulphur atom;
$R^{13}$ stands for cyano group;
X means —NH— group;
n is a value of 1;
and their salts, solvates, N-oxides and isomers and the salts and solvates thereof.

An even narrower group of the compounds of the general formula (I) is formed by those,
wherein
$R^1$ stands for hydrogen atom;
$R^2$ stands for hydrogen atom;
$R^3$ stands for a phenyl group, or
a 6-membered heterocyclic ring containing one nitrogen atom;
$R^4$ stands for a 6-membered heterocyclic ring containing one nitrogen atom, or
a group of the general formula (b), wherein
$R^8$ and $R^9$ stand for methyl group;
Z means oxygen atom, or —$NR^{12}$— group—where $R^{12}$ stands for hydrogen atom, methyl group, or acetyl group;
W means nitrogen atom;
m is a value of 2;
o is a value of 2;
p is a value of zero or 1;
r is a value of zero or 1;
t is a value of zero;

$R^5$ stands for a phenyl group, optionally substituted with methoxy group, hydroxyl group, or halogen atom, or
a 5- or 6-membered heterocyclic ring containing one nitrogen atom, or one nitrogen atom and one sulphur atom;
$R^{13}$ stands for cyano group;
X means —NH— group;
n is a value of 1;
and their salts, solvates, N-oxides and isomers and the salts and solvates thereof.

Representatives of the compounds of general formula (I) are e.g. the following compounds:
2-(3-methoxyphenyl)-7-(morpholin-4-yl)-9-benzylamino-10-cyano-s-triazolo[1,5-a]quinoline,
2-(4-methoxyphenyl)-7-(morpholin-4-yl)-9-benzylamino-10-cyano-s-triazolo[1,5-a]quinoline,
2-(4-methoxyphenyl)-7-(2,6-trans-dimethylmorpholin-4-yl)-9-benzylamino-10-cyano-s-triazolo[1,5-a]quinoline,
2-(pyridin-4-yl)-7-(4-methylpiperazin-1-yl)-9-benzylamino-10-cyano-s-triazolo[1,5-a]quinoline,
2-(4-methoxyphenyl)-7-(4-methylpiperazin-1-yl)-9-benzylamino-10-cyano-s-triazolo[1,5-a]quinoline,
2-(3-methoxyphenyl)-7-(4-methylpiperazin-1-yl)-9-benzylamino-10-cyano-s-triazolo[1,5-a]quinoline,
2-(3-hydroxyphenyl)-7-(4-methylpiperazin-1-yl)-9-benzylamino-10-cyano-s-triazolo[1,5-a]quinoline,
2-(3-methoxphenyl)-7-(4-acetylpiperazin-1-yl)-9-benzylamino-10-cyano-s-triazolo[1,5-a]quinoline,
2-(3-metoxifenil)-7-(piperazin-1-il)-9-benzilamino-10-ciano-s-triazolo[1,5-a]quinoline,
2-phenyl-7-(pyridin-3-yl)-9-benzylamino-10-cyano-s-triazolo[1,5-a]quinoline,
2-phenyl-7-(4-methylpiperazin-1-yl)-9-(2-pyridylmethylamino)-10-cyano-s-triazolo[1,5-a]quinoline, 2-(3-methoxyphenyl)-7-(pyridin-3-yl)-9-(4-pyridylm-
ethylamino)-10-cyano-s-triazolo[1,5-a]quinoline, and their salts, solvates, N-oxides and isomers and the salts and solvates thereof.

Representatives of the salts of the compounds of general formula (I) are e.g. the following compounds:

2-(3-methoxyphenyl)-7-(morpholin-4-yl)-9-benzy-
lamino-10-cyano-s-triazolo[1,5-a]quinoline hydrochloride, 2-(4-methoxyphenyl)-7-(morpholin-4-yl)-9-benzy-
lamino-10-cyano-s-triazolo[1,5-a]quinoline hydrochloride, 2-(4-methoxyphenyl)-7-(2,6-dimethylmorpholin-4-yl)-9-
benzylamino-10-cyano-s-triazolo[1,5-a]quinoline
hydrogensulfate, 2-(pyridin-4-yl)-7-(4-methylpiperazin-1-yl)-9-benzy-
lamino-10-cyano-s-triazolo[1,5-a]quinoline maleate, 2-(4-methoxyphenyl)-7-(4-methylpiperazin-1-yl)-9-ben-
zylamino-10-cyano-s-triazolo[1,5-a]quinoline-hemifu-
marate monohydrate, 2-(3-methoxyphenyl)-7-(4-methylpiperazin-1-yl)-9-ben-
zylamino-10-cyano-s-triazolo[1,5-a]quinoline-hemifu-
marate hemihydrate, 2-(3-hydroxyphenyl)-7-(4-methylpiperazin-1-yl)-9-ben-
zylamino-10-cyano-s-triazolo[1,5-a]quinoline hydrochloride, 2-(3-Methoxyphenyl)-7-(4-acetylpiperazin-1-yl)-9-ben-
zylamino-10-cyano-s-triazolo[1,5-a]quinoline hydrogensulfate, 2-(3-methoxyphenyl)-7-(piperazin-1-yl)-9-benzylamino-
10-cyano-s-triazolo[1,5-a]quinoline maleate, 2-Phenyl-7-(pyridin-3-yl)-9-benzylamino-10-cyano-s-
triazolo[1,5-α]quinoline hydrogensulfate, 2-phenyl-7-(4-methylpiperazin-1-yl)-9-(2-pyridylmethy-
lamino)-10-cyano-s-triazolo[1,5-α]quinoline hydrochloride, 2-(3-Methoxyphenyl)-7-(pyridin-3-yl)-9-(4-pyridylm-
ethylamino)-10-cyano-s-triazolo[1,5-α]quinoline
hydrogensulfate.

According to another of its aspects, the present invention also relates to pharmaceutical compositions containing as active principles the compounds of the general formula (I) or their isomers, salts and solvates, which are preferably oral compositions, but inhalable, parenteral and transdermal formulations are also subjects of the invention. The above pharmaceutical compositions may be solids or liquids, such as tablets, pellets, capsules, patches, solutions, suspensions or emulsions. The solid compositions, first of all tablets and capsules are the preferred pharmaceutical forms.

The above pharmaceutical compositions are prepared by applying pharmaceutical excipients commonly used in the pharmaceutical industry and by usual technological operations.

The compounds of the general formula (I) according to the present invention can be used for the treatment of pathologies, where $A_3$ receptor plays a role in the development of the disease.

The compounds which have a selective effect on the $A_3$ receptor may be useful in the treatment and/or prevention of disfunctions of the heart (Y. Guo et al., J Mol Cell Cardiol. 2001, 33:825-30, R. G. Black et al. Circ Res. 2002, 91:165-72.), eye, the kidney (H. T. Lee et al. Am J Physiol Regul Integr Comp Physiol. 2006, 291:R959-69), the respiratory system, joints (L. Madi J Rheumatol. 2007, 34:20-6) the gastrointestinal tract (L. Antonioli et al. Inflamm Bowel Dis. 2007 Nov. 16, L. Rybaczyk et al. Gastroenterology 2007; 132(Suppl 2):A-246) and the central nervous system (G. J Chen et al. J Neurosci Res. 2006, 84:1848-55). They inhibit the degranulation of the mast cells, inhibit the production of the cytokines, decrease the inner pressure in the eyes, the liberation of TNFα, hinder the migration and activation of the eozinofil and neutrofil granulocytes, and of other inflammation cells, inhibit the constriction of the airway smooth muscles and hinder infiltration of the blood plasma through the blood-vessel. By inhibiting the adenosine $A_3$ receptor, pathologies which are related to increased mucin production (e.g. asthma and COPD), can be healed.

Mast cells play a key role in the pathomechanism of not only allergy, asthma but Irritable Bowel Syndrome (IBS) too. Mast cells translate the stress signals that has been transmitted through brain gut axis into release of proinflammatory mediators that can cause stimulation of nerve endings that could affect afferent nerve terminals and change their perception, affect intestinal motility, increase intestinal perpermeability and, in susceptible individuals, modulate the inflammation (World J Gastroenterol. 2007, 22:3027-30). A subset of patients IBS have an increased number of mast cells in the colonic mucosa (Gut 2008, 57:468-473). Moreover, activated mast cells in proximity to colonic nerves correlate with abdominal pain and visceral hypersensitivity in patients with diarrhea in IBS (Gastroenterology 2004, 126:693-702, J Gastroenterol Hepatol 2006, 21(1 Pt 1):71-8.). Mast cells are under the both paracrine and autocrine regulation of adenosine partly through mast cell adenosine A3 receptor.

Based on the above effects, adenosine $A_3$ receptor antagonists may be therapeutically useful as antiasthmatic, antiischemic, antidepressant, antiarrhythmic, antirheumatic, antiglaucomic, antiinflammatory in inflammatory and irritable bowel diseases, antiCOPD, kidney function protective, tumor preventing, antiparkinson and cognitive function stimulating medicaments. They may also be useful in the treatment or prevention of the following diseases: injury of the heart muscle during reperfusion, acute respiratory distress syndrome (ARDS), chronic obstructive pulmonary disease (COPD)—including chronic bronchitis, pulmonary emphysema or difficult breathing—, allergic reactions (e.g. rhinitis, poison ivy-induced responses, nettle-rush, scleroderma, arthritis), other autoimmune diseases, inflammatory bowel diseases (IBD)—including Crohn disease and ulcerative colitis—, irritable bowel syndrome (IBS), Addison disease, psoriasis, diseases of the joints, hypertonia, abnormal neurological functions, glaucoma and diabetes (Naunyn-Schmiedberg's Arch. Pharmacol. 362:382, 2000; TiPS 21:456, 2000, Am. J. Resp. Cell Mol. Biol. 35: 549, 2006).

The compounds of the present invention can favourably be used in the treatment of disfunctions like asthma (Clin. Exp. Allergy 32:824, 2002; J. Allergy. Clin. Immuno., 114:737, 2004), COPD (Am. J. Respir. Crit. Care Med., 173:398, 2006), ARDS, glaucoma (Investigative Opthalmology & Visual Science, Vol. 46, 2005,), tumor, IBD, IBS (World J. Gastroenterol. 2007, 22:3027-30.), allergic and inflammatory pain (Pain 121:105, 2006), rheumatoid arthritis (J. Rheumatol. 34:20-6, 2007), ischemia, hypoxia, arrhythmia of the heart, diseases of the kidney and mood diseases (JPET Fast Forward. Published on Apr. 25, 2007 as DOI:10.1124/jpet.107.121665).

According to another of its aspects, the present invention relates to the use of the compounds of the general formula (I) in the treatment of the above pathologies. Suggested daily dose is 1-100 mg active ingredient depending on the nature and severeness of the disease and on sex, weight etc. of the patient.

A further subject of the invention is the preparation of the compounds of the general formula (I) and of the intermediates of the general formulae (II), (III), (V), (VI), (IX), (X), (XI), (XII), (XIV) and (XV).

A part of the intermediates of the general formulae (II), (III), (V), (VI), (IX), (X), (XI), (XII), (XIV) and (XV) used in the process according to the invention is novel.

Process A) of our invention is outlined in reaction scheme 1 (FIG. 1).

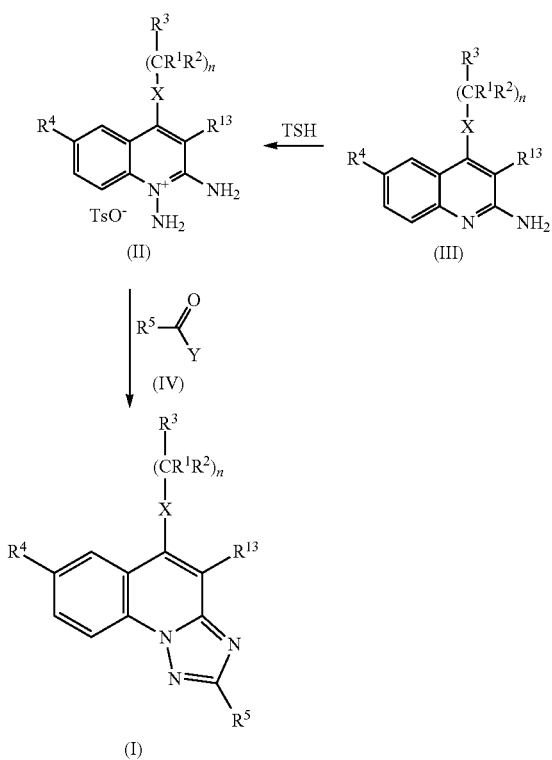

wherein—the meaning of $R^5$ is as given above and Y stands for hydrogen atom, halogen atom or $C_{1-4}$ alkoxy group—preferably with the appropriate acid chlorides or esters (D. W. Robertson, J. Med. Chem., 28, 717, 1985) and if desired, the substituents of the compound of the general formula (I) are transformed into each other by a method known per se, and/or the resulting compound of the general formula (I) is transformed into its salt, solvate, N-oxide or liberated from its salt, solvate, and/or is resolved into its optically active isomers, or the optically active isomer is transformed into the racemic compound, and if desired the structural isomers are separated. Aldehydes can also be used for the ring closure. As cyclising agent, preferably triethylamine in dimethylformamide can be applied, but other agents of that type, known from the organic chemistry can also be used. The cyclisation can be performed in a wide range of temperature, preferably between 20° C.-150° C.

Process B) of our invention is outlined in reaction scheme 2 (FIG. 2).

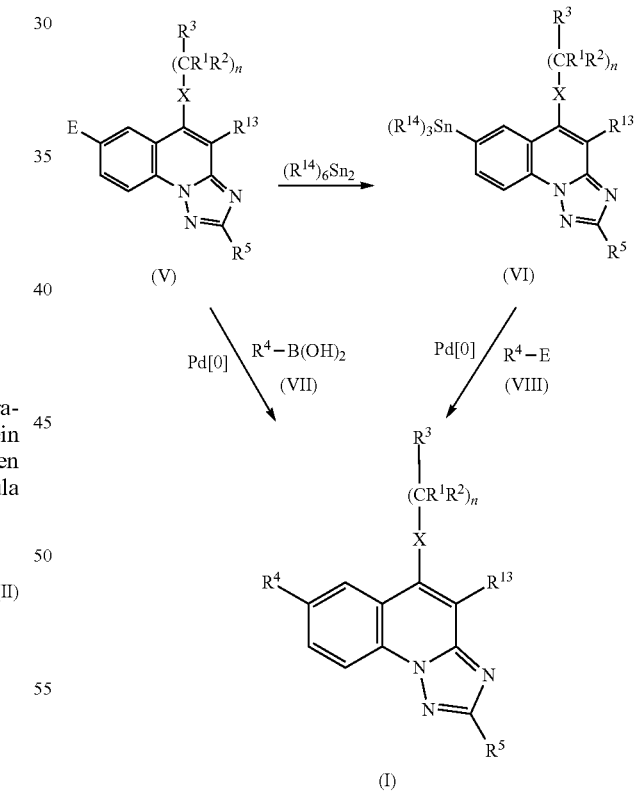

According to Process A) of our invention for the preparation of the compounds of the general formula (I)—wherein $R^1$, $R^2$, $R^3$, $R^4$, $R^5$, $R^{13}$, X and n have the meanings as given above—a 1,2-diamino-azinium salt of the general formula (II)

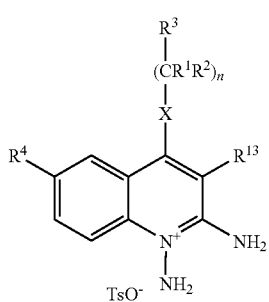

wherein $R^1$, $R^2$, $R^3$, $R^4$, $R^{13}$, X and n have the meanings as given above and TsO⁻ means p-toluene-sulfonate anion—is reacted with a compound of the general formula (IV), According to our invention for the preparation of the compounds of the general formula (I)—where
$R^4$ means phenyl-, benzyl-, thienyl-, or furyl group substituted with methylenedioxy group or with one or more, identical or different, straight or branched $C_{1-4}$ alkyl group, straight or branched $C_{1-4}$ alkoxy group, hydroxyl group, trifluoromethyl group, cyano group or halogen atom, or a 5- or 6-membered heterocyclic ring linked through a carbon atom, containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (b), where if the value of t is 1, then W means nitrogen atom or —CH— group, or if the value of t is 0, then W means —CH— group, and the meanings of Z, m, o, p, r, $R^8$ and $R^9$ are as defined above, and the meanings of $R^1$, $R^2$, $R^3$, $R^5$, $R^{13}$, X and n, are as defined above, in process B/1) the triazole derivative of the general formula (V),

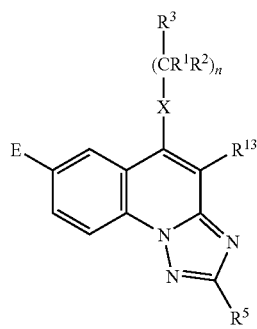

(V)

where E stands for halogen atom or trifluoromethanesulfonyl group, and the meanings of $R^1$, $R^2$, $R^3$, $R^5$, $R^{13}$, X and n are as defined above, and a compound of the general formula (VII),

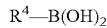 (VII)

where the meaning of $R^4$ is as defined above for process B) are reacted under the conditions of the Suzuki reaction (A. Kotschy, G. Timári: *Heterocycles from Transition Metal Catalysis*. Springer, 2005), or in process B/2) a trialkyltin-triazole derivative of the general formula (VI),

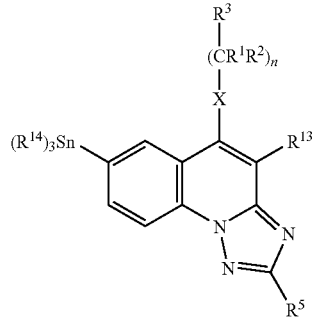

(VI)

where $R^{14}$ stands for a straight or branched $C_{1-4}$ alkyl group and the meanings of $R^1$, $R^2$, $R^3 R^5$, $R^{13}$, X and n are as defined above, and compound of the general formula (VIII),

 (VIII)

where E stands for halogen atom or trifluoromethanesulfonyl group and the meaning of $R^4$ is as defined above for process B) are reacted under the conditions of the a Stille reaction (A. Kotschy, G. Timári: *Heterocycles from Transition Metal Catalysis*. Springer, 2005);

and if desired, the substituents of the compound of the general formula (I) are transformed into each other by a method known per se, and/or the resulting compound of the general formula (I) is transformed into its salt, solvate, N-oxide or liberated from its salt, solvate, and/or is resolved into its optically active isomer, or the optically active isomer is transformed into the racemic compound, and if desired the structural isomers are separated.

Process C) of our invention is outlined in reaction scheme 3 (FIG. 3).

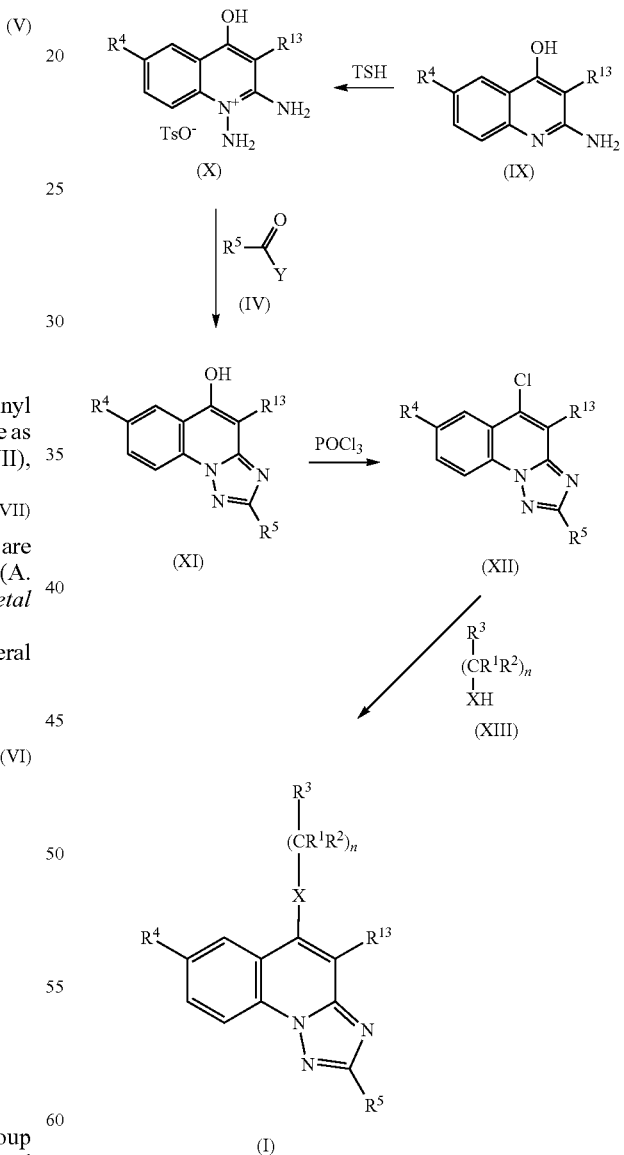

FIG. 3

According to process C) of our invention, for the preparation of the compounds of the general formula (I)—where the meanings of $R^1$, $R^2$, $R^3$, $R^4$, $R^5$, $R^{13}$, X and n are as defined above—a triazole derivative of the general formula (XII),

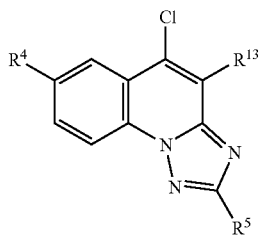
(XII)

where the meanings of $R^4$, $R^5$ and $R^{13}$ are as defined above, and a compound of the general formula (XIII),

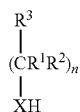
(XIII)

where the meanings of X, $R^1$, $R^2$ and $R^3$ and n are as defined above—are reacted by a method known per se (Nan Zhang, Bioorg. and Med. Chem. Lett., 10, 2825, 2000) and if desired, the substituents of the compound of the general formula (I) are transformed into each other by a method known per se, and/or the resulting compound of the general formula (I) is transformed into its salt, solvate, N-oxide or liberated from its salt, solvate, and/or is resolved into its optically active isomer, or the optically active isomer is transformed into the racemic compound, and if desired the structural isomers are separated.

Process D) of our invention is outlined in reaction scheme 4 (FIG. 4).

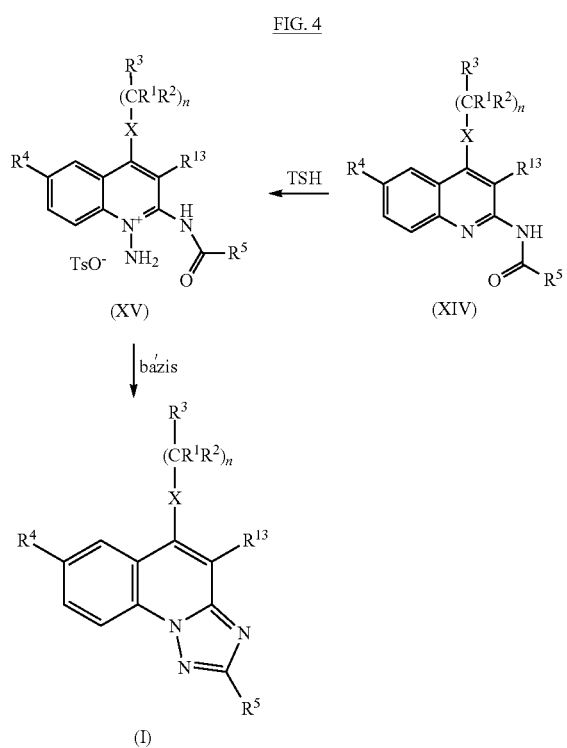

FIG. 4

According to process D) of our invention, for the preparation of the compounds of the general formula (I)—where the meanings of $R^1$, $R^2$, $R^3$, $R^4$, $R^5$, $R^{13}$, X and n are as defined above—we can also use a compound of the general formula (XV),

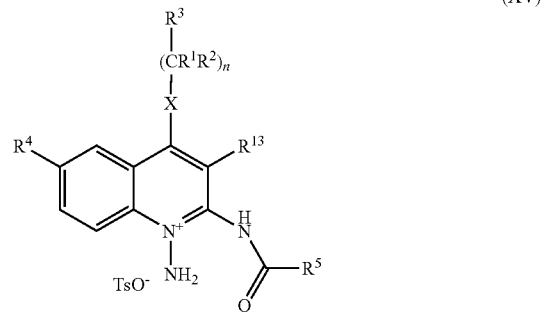
(XV)

where the meanings of X, $R^1$, $R^2$, $R^3$, $R^4$, $R^5$, $R^{13}$ and n are as defined above and TsO⁻ means p-toluenesulfonate anion—is cyclized in the presence of an organic or inorganic base, preferably triethylamine or pyridine, and if desired, the substituents of the compound of the general formula (I) are transformed into each other by a method known per se, and/or the resulting compound of the general formula (I) is transformed into its salt, solvate, N-oxide or liberated from its salt, solvate, and/or is resolved into its optically active isomer, or the optically active isomer is transformed into the racemic compound, and if desired the structural isomers are separated.

The starting materials used in the above processes and their preparations are demonstrated as follows.

The compounds of the general formula (II)—

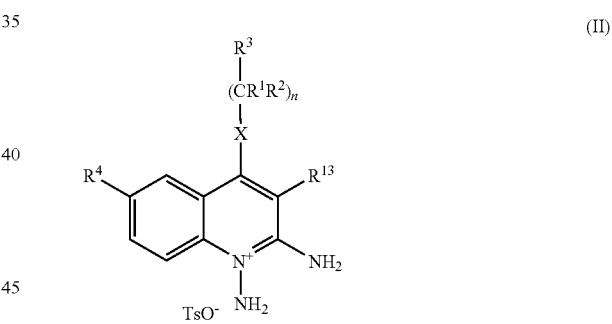
(II)

where the meanings of $R^1$, $R^2$, $R^3$, $R^4$, $R^{13}$ and n are as defined above and TsO⁻ means p-toluenesulfonate anion—are new materials and they can be prepared by several known methods, among others e.g. as outlined in reaction scheme 1 (FIG. 1), from a compound of the general formula (III),

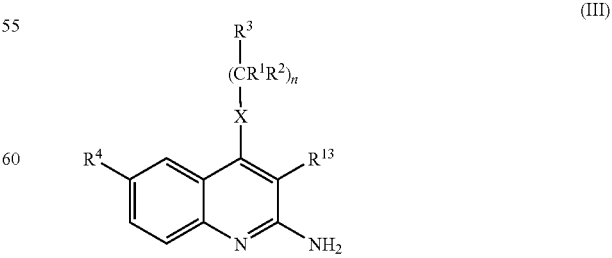
(III)

where the meanings of X, $R^1$, $R^2$, $R^3$, $R^4$, $R^{13}$ and n are as defined above—by the N-amination reaction known in the organic chemistry (E. E. Glover, R. T. Rowbotton, J. Chem.

Soc. Perkin Trans I., 376, 1976; G. Timári, Gy. Hajós, S. Bátori and A. Messmer, Chem. Ber., 125, 929, 1992). As for N-amination agent preferably O-tosyl-hydroxylamine (TSH) is applied, but other compounds known as N-amination agents can also be used.

The compounds of the general formula (III) are partly known from the patent application of publication number WO 2005/009969 or they can be prepared by analogy with the method described therein.

Those compounds of the general formula (III), where $R^4$ stands for a phenyl-, benzyl-, thienyl-, or furyl group, substituted with methylenedioxy group, or one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring linked through a carbon atom, containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (b), where if the value of t is 1, then W stands for nitrogen atom or —CH— group, or if the value of t is 0, W stands for —CH— group, and the meanings of Z, m, o, p, r, $R^8$ and $R^9$ are as defined above, and the meanings of $R^1$, $R^2$, $R^3$, $R^5$, $R^{13}$, X and n are as defined above can be prepared analogously to the process version B/1) of the invention by using a 6-halogeno-aminoquinoline derivative known from patent application WO 02/096879 or its analogues, as starting material.

Those compounds of the general formula (V),

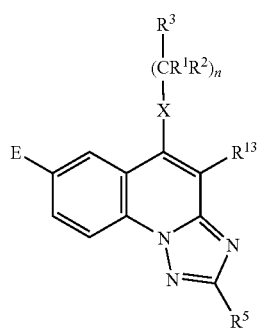

(V)

where E stands for halogen atom and the meanings of $R^1$, $R^2$, $R^3$, $R^5$, $R^{13}$, X and n are as defined above are partly known from international patent application of publication number WO 03/053968 or can be prepared by analogy with the method described therein.

Those compounds of the general formula (V), where E stands for trifluoromethanesulfonyl group and the meanings of $R^1$, $R^2$, $R^3$, $R^5$, $R^{13}$, X and n are as defined above, can be prepared from the appropriate compounds described in international patent application of publication number WO 03/053968 or from their analogues, containing a hydroxyl group for group E, by a method known from the organic chemistry (G. Timári, T. Soós, Gy. Hajós, A. Messmer, J. Nacsa and J. Molnár, Bioorg. Med. Chem. Lett, 2831, 1996).

The compounds of the general formula (VI),

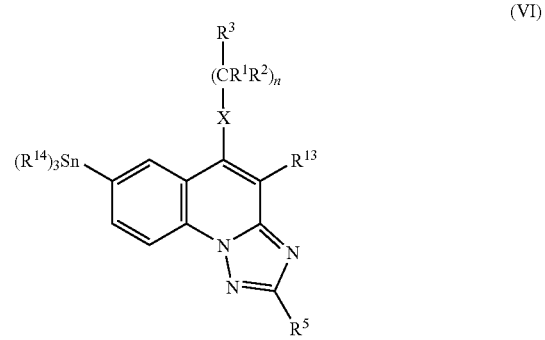

(VI)

where $R^{14}$ stands for straight or branched $C_{1-4}$ alkyl group and the meanings of $R^1$, $R^2$, $R^3$, $R^5$, $R^{13}$, X and n are as defined above, are new compounds. The intermediates of the general formula (VI) can be prepared by several known methods, e.g. according to reaction scheme 2 (FIG. 2), from a compound of the general formula (V) by processes known in the organic chemistry (A. Kotschy, G. Timári: *Heterocycles from Transition Metal Catalysis*. Springer, 2005, WO 2006/051341). To build the trialkylstannate group, preferably hexamethyldistannate is used.

The compounds of the general formula (XII),

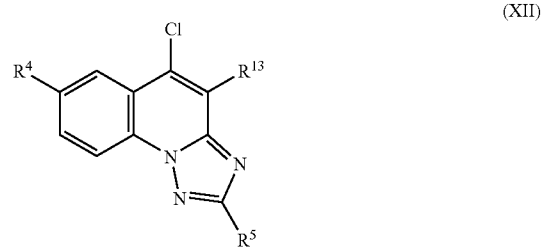

(XII)

where the meanings of $R^4$, $R^5$ and $R^{13}$ are as defined above—are new compounds. The compounds of the general formula (XII)—where the meanings of $R^4$, $R^5$ and $R^{13}$ are as defined above—can be prepared from a compound of the general formula (XI),

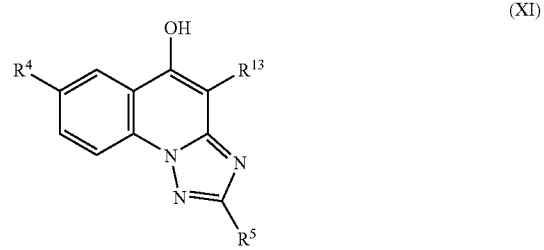

(XI)

where the meanings of $R^4$, $R^5$ and $R^{13}$ are as defined above—by methods known per se (D. L. Leysen, J. Heterocyclic Chem., 24, 1611, 1987) according to reaction scheme 3 (FIG. 3).

The compounds of the general formula (XI)—where the meanings of $R^4$, $R^5$ and $R^{13}$ are as defined above—are new compounds. For their preparation a 1,2-diamino-azinium salt of the general formula (X),

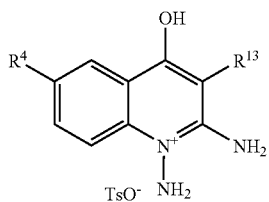

(X)

where the meanings of $R^4$ and $R^{13}$ are as defined above and TsO⁻ stands for p-toluenesulfonate anion—are reacted with a compound of the general formula (IV),

(IV)

where the meanings of $R^5$ is as defined above and Y stands for hydrogen atom, halogen atom or a $C_{1-4}$ alkoxy group, preferably with the appropriate acid chlorides or esters (D. W. Robertson, J. Med. Chem., 28, 717, 1985). Aldehydes can also be used for the ring closure.

As cyclising agent preferably triethylamine in dimethylformamide is applied, but other agents of the type, known from the organic chemistry can also be used. The cyclisation can be performed in a wide range of temperature, preferably between 20° C.-150° C.

The compounds of the general formula (X)—where the meanings of $R^4$ and $R^{13}$ are as defined above—are new compounds, they can be prepared by several known methods, e.g. according to reaction scheme 3 (FIG. 3), from a compound of the general formula (IX),

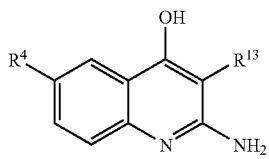

(IX)

where the meanings of $R^4$ and $R^{13}$ are as defined above, by the N-amination reaction known in the organic chemistry (E. E. Glover, R. T. Rowbotton, J. Chem. Soc. Perkin Trans I., 376, 1976, G. Timári, Gy. Hajós, S. Bátori and A. Messmer, Chem. Ber., 125, 929, 1992). As for N-amination agent preferably O-tosyl-hydroxylamine (TSH) is applied, but other compounds known as N-amination agents can also be used.

The compounds of the general formula (IX) are partly known from international patent application of publication number WO 2005/009969 or can be prepared by analogy with the method described in international patent application of publication number WO 2005/009969, starting from the 2-nitrobenzoic acid containing the appropriate $R^4$ substituent in position-5.

The compounds of the general formula (XV),

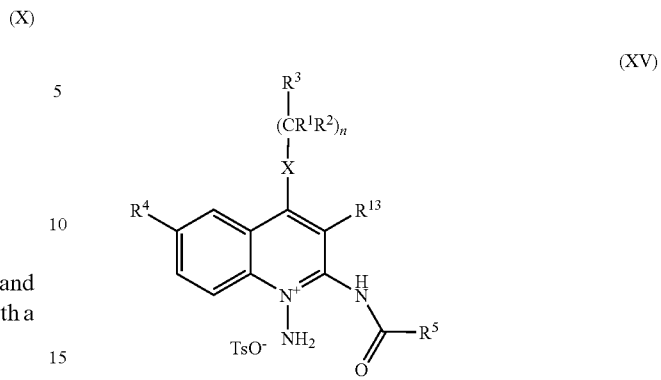

(XV)

where X, $R^1$, $R^2$, $R^3$, $R^4$, $R^5$, $R^{13}$ and n have the meanings as defined above and TsO⁻ means p-toluenesulfonate anion—are new compounds. The intermediates of the general formula (XV) can be prepared by several known methods, e.g. according to reaction scheme 4 (FIG. 4), from a compound of the general formula (XIV),

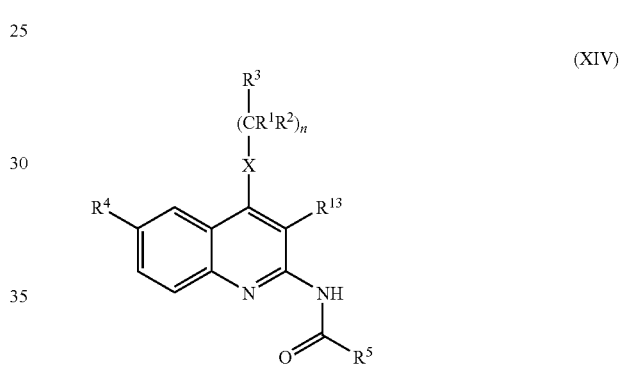

(XIV)

where the meanings of X, $R^1$, $R^2$, $R^3$, $R^4$, $R^5$, $R^{13}$ and n are as defined above, by the N-amination reaction known in the organic chemistry (E. E. Glover, R. T. Rowbotton, J. Chem. Soc. Perkin Trans I., 376, 1976, G. Timári, Gy. Hajós, S. Bátori and A. Messmer, Chem. Ber., 125, 929, 1992). As N-amination agent preferably O-tosyl-hydroxylamine (TSH) is applied, but other compounds known as N-amination agents can also be used.

The compounds of the general formula (XIV) are partly known from international patent application of publication number WO 2005/009969 or can be prepared by analogy with the method described in patent application of publication number WO 2005/009969, from the compounds of the general formula (III).

General procedure for preparation of N-oxides:

The appropriate amine was dissolved in chloroform and excess of mCPBA was added in portion. After stirring at room temperature for 5 hours the reaction mixture was extracted with 10% sodiumcarbonate solution and the organic layer was evaporated. The solid residue was purified by chromatography to give the desired N-oxides.

General procedure for preparation of the salts:

To the solution of appropriate base, dissolved in tetrahydrofurane, an ethanolic solution of 1.2 equivalent of acid (hydrochloric acid, sulphuric acid, fumaric acid, maleic acid) was added and stirred at room temperature. The resulting precipitate was filtered off and washed with cold ethanol give the desired salts.

The compounds according to the invention of the general formulae (I) (II), (III), (V), (VI), (IX), (X), (XI), (XII), (XIV) and (XV), their preparation, and the biological activity of the compounds of the general formula (I) are demonstrated in the examples below, without limiting the claims to the examples.

EXAMPLES

Example 1

2-(3-methoxyphenyl)-7-(morpholin-4-yl)-9-benzylamino-10-cyano-s-triazolo[1,5-a]quinoline In the general formula (I) $R^1$ and $R^2$ stands for hydrogen atom, $R^3$ stands for phenyl group, $R^5$ stands for 3-methoxyphenyl group, $R^4$ means group (b), where W stands for nitrogen atom, Z stands for oxygen atom, the value of m and o is 2, the value of r, p and t is 0, $R^{13}$ stands for cyano group, X stands for NH group and the value of n is 1.

a.) 1,2-diamino-3-cyano-4-benzylamino-6-(morpholin-4-yl)quinolinium tosylate

To the solution of 3 g 2-amino-3-cyano-4-benzylamino-6-morpholino-quinoline in 20 ml dimethylformamide, 2.2 g of O-tosylhydroxylamine dissolved in 25 ml dichloromethane is added dropwise at 20° C. in 15 minutes. After 5 hours of stirring the precipitated crystalline material is filtered off. After drying 3.8 g of the title compound is obtained ($MH^+$: 376).

b.) 2-(3-methoxyphenyl)-7-(morpholin-4-yl)-9-benzylamino-10-cyano-s-triazolo[1,5-a]quinoline 3.5 g 1,2-diamino-3-cyano-4-benzylamino-6-(morpholin-4-yl)quinolinium tosylate is dissolved in 50 ml ethanol and to the solution are added 12 ml of 1 mol/liter concentration sodium ethylate in ethanol solution and 2 g of 3-methoxybenzaldehyde. The reaction mixture is heated at reflux temperature for 4 hours. The precipitated crystalline material is filtered off and recrystallized from dimethylformamide. After drying 1.8 g of the title compound is obtained ($MH^+$:491).
$^1$H-NMR (DMSO-$d_6$), δ, ppm: 8.68 (br, 1H); 8.23(d, 1H); 7.79-7.64 (m, 4H); 7.43-7.05 (m, 7H); 5.15 (d. 2H); 3.84 (s, 3H); 3.80-3.78 (m, 4H); 3.32-3.30 (m, 4H).

Example 1.2

2-(3-methoxyphenyl)-7-(morpholin-4-yl)-9-benzylamino-10-cyano-s-triazolo[1,5-a]quinoline hydrochloride To the solution of 0.4 g 2-(3-methoxyphenyl)-7-(morpholin-4-yl)-9-benzylamino-10-cyano-s-triazolo[1,5-a]quinoline in 30 ml ethyl acetate, 5 ml of 4 mol/liter concentration hydrogen chloride in ether solution is added. The precipitated crystalline material is filtered off. After drying 0.42 g of the title compound is obtained ($MH^+$:491).
$^1$H-NMR (DMSO-$d_6$), δ, ppm: 8.68 (br, 1H); 8.23(d, 1H); 7.82-7.64(m, 4H); 7.43-7.05(m, 7H); 5.15(d. 2H); 3.84(s, 3H); 3.82-3.78(m, 4H); 3.43-3.30(m, 4H)

Example 2

2-(4-methoxyphenyl)-7-(morpholin-4-yl)-9-benzylamino-10-cyano-s-triazolo[1,5-a]quinoline In the general formula (I) $R^1$ and $R^2$ stand for hydrogen atom, $R^3$ stands for phenyl group, $R^5$ stands for 4-methoxyphenyl group, $R^4$ means group (b), where W stands for nitrogen atom, Z stands for oxygen atom, the value of m and o is 2, the value of r, p and t is 0, $R^{13}$ stands for cyano group, X stands for NH group and the value of n is 1.

a.) 2-(4-methoxyphenyl)-7-(morpholin-4-yl)-9-benzylamino-10-cyano-s-triazolo[1,5-a]quinoline To the solution of 3.5 g 1,2-diamino-3-cyano-4-benzylamino-6-(morpholin-4-yl)quinolinium tosylate in 50 ml ethanol, described in Example 1., 12 ml of 1 mol/liter concentration sodium ethylate in ethanol solution and 2 g of 4-methoxybenzaldehyde are added. The reaction mixture is heated at reflux temperature for 4 hours. The precipitated crystalline material is filtered off and recrystallized from dimethylformamide. After drying, 1.65 g of the title compound is obtained ($MH^+$:491).
$^1$H-NMR (DMSO-$d_6$), δ, ppm: 8.72 (br, 1H); 8.23(d, 1H); 7.79-7.64(m, 4H); 7.43-7.05(m, 7H); 5.13(d. 2H); 3.94(s, 3H); 3.80-3.78(m, 4H); 3.32-3.30(m, 4H)

Example 2.2

2-(4-methoxyphenyl)-7-(morpholin-4-yl)-9-benzylamino-10-cyano-s-triazolo[1,5-a]quinoline hydrochloride Title compound is prepared by the general method disclosed above by adding a solution of hydrochloric acid to the compound prepared according to Example 2.
$^1$H-NMR (DMSO-$d_6$), δ, ppm: 8.81 (br, 1H); 8.33(d, 1H); 7.82-7.64(m, 4H); 7.43-7.05(m, 7H); 5.15(d. 2H); 3.96(s, 3H); 3.80-3.78(m, 4H); 3.36-3.32(m, 4H)

Example 3

2-(4-methoxyphenyl)-7-(2,6-dimethylmorpholin-4-yl)-9-benzylamino-10-cyano-s-triazolo[1,5-a]quinoline In the general formula (I) $R^1$ and $R^2$ stand for hydrogen atom, $R^3$ stands for phenyl group, $R^5$ stands for 4-methoxyphenyl group, $R^4$ means group (b), where W stands for nitrogen atom, Z stands for oxygen atom, the value of m and o is 2, the value of r and p is 1, $R^8$ and $R^9$ stand for methyl group, the value of t is 0, $R^{13}$ stands for cyano group, X stands for NH group and the value of n is 1.

a.) 2-Nitro-5-(2,6-dimethylmorpholin-4-yl)benzoic acid

The mixture of 5 g 2-nitro-5-chlorobenzoic acid and 15 ml 2,6-dimethylmorpholine is stirred at 120° C. for 6 hours. To the reaction mixture 150 ml of ethyl acetate is added. The precipitated yellow crystalline material is filtered off, dissolved in 15 ml water. The pH of the mixture is set to 6 with acetic acid. The precipitated material is filtered off, washed with water and dried, to obtain 4.2 g of the title compound ($MH^+$:281).

b.) 2-Amino-5-(2,6-dimethylmorpholin-4-yl)benzoic acid

The mixture of 6 g 2-nitro-5-(2,6-dimethylmorpholin-4-yl)benzoic acid, 15 ml cyclohexene and 3 g Pd/C (10%) is heated under reflux for 6 hours. The hot reaction mixture is filtered through a celite pad. After evaporation of the filtrate 4.8 g title product is obtained (MH⁺: 251).

c.) 5-(2,6-dimethylmorpholin-4-yl)isatoic anhydride

To the mixture of 8.9 g of 2-amino-5-(2,6-dimethylmorpholin-4-yl)benzoic acid in 60 ml of dioxane, under stirring and external cold water cooling 10 ml of diphosgene is added dropwise. The mixture is heated under reflux conditions for 4 hours. From the cold reaction mixture the solid material is filtered off, washed with 50 ml of ether. The product is stirred for 5 minutes in the mixture of 50 ml of methanol and 5 ml of triethylamine, then filtered off and washed with 30 ml of methanol. After drying 7 g of the title product is obtained (MH⁺: 277).

d.) 2-Amino-3-cyano-4-hydroxy-6-(2,6-dimethyl-morpholin-4-yl)quinoline 4 g of malonitrile is dissolved in 50 ml of dimethylformamide. To the solution, in several portions, 2.4 g of 60% sodium hydride in oily dispersion are added. To the clear solution 8 g of 5-(2,6-dimethylmorpholin-4-yl)isatoic anhydride is added and the mixture is stirred at room temperature for 10 hours. The reaction mixture is diluted with 70 ml of water and extracted with 2×30 ml of ethyl acetate. The aqueous phase is evaporated in vacuum, the solid residue is dissolved in 20 ml of water, and the pH is set to 6. The precipitated material is filtered off, washed with water. After drying 6.5 g of the title compound is obtained. (MH⁺: 299)

e.) 2-Amino-3-cyano-4-chloro-6-(2,6-dimethylmorpholin-4-yl)quinoline

The mixture of 1.7 g of 2-amino-3-cyano-4-hydroxy-6-(2,6-dimethylmorpholin-4-yl)quinoline and 3.4 ml of phosphoryl chloride is stirred at 120° C. for 4 hours. The cooled reaction mixture is poured onto 30 g of ice, the pH of the mixture is adjusted to 8 with 10% sodium hydroxide solution, and the precipitated material is filtered off. After drying 1.5 g of the title compound is obtained (MH⁺: 317).

f.) 2-Amino-3-cyano-4-benzylamino-6-(2,6-dimethylmorpholin-4-yl)quinoline 3 g of 2-amino-3-cyano-4-chloro-6-(2,6-dimethylmorpholin-4-yl)quinoline and 6 ml of benzylamine are stirred at 125° C. for 3 hours. The reaction mixture is poured onto 30 ml of water. The precipitated material is filtered off, washed with 20 ml of water. After drying 2.3 g of the title compound is obtained (MH⁺: 388).

g.) 1,2-diamino-3-cyano-4-benzylamino-6-(2,6-dimethylmorpholin-4-yl)quinolinium tosylate To the solution of 3.2 g of 2-amino-3-cyano-4-benzylamino-6-(2,6-dimethylmorpholin-4-yl)quinoline in 20 ml dimethylformamide, 2.2 g of O-tosylhydroxylamine in 25 ml dichloromethane is dropped at 20° C. in 15 minutes. After 5 hours of stirring the precipitated crystalline material is filtered off. After drying 3.4 g of the title compound is obtained (MH⁺:403).

h.) 2-(4-methoxyphenyl)-7-(2,6-dimethylmorpholin-4-yl)-9-benzylamino-10-cyano-s-triazolo[1,5-a]quinoline 3.5 g of 1,2-diamino-3-cyano-4-benzylamino-6-(2,6-dimethylmorpholin-4-yl)quinolinium tosylate is dissolved in 50 ml ethanol and to this solution 12 ml of 1 mol/l concentration sodium ethylate in ethanol solution and 2 g of 4-methoxybenzaldehyde are added. The reaction mixture is heated at reflux temperature for 4 hours. The precipitated crystalline material is filtered off and recrystallized from dimethylformamide. After drying 1.85 g of the title compound is obtained (MH⁺: 518).

¹H-NMR (DMSO-d₆), δ, ppm: 8.70 (br, 1H); 8.26(d, 1H); 7.89-7.64(m, 4H); 7.43-7.15(m, 7H); 5.16(d. 2H); 3.90(s, 3H); 3.77-3.74(m, 4H); 2.41-2.38(m, 2H); 1.2(d, 6H)

Example 3.2

2-(4-methoxyphenyl)-7-(2,6-dimethylmorpholin-4-yl)-9-benzylamino-10-cyano-s-triazolo[1,5-a]quinoline hydrogensulfate Title compound is prepared by the general method disclosed above by adding a solution of sulphuric acid to the compound prepared according to Example 3.

¹H-NMR (DMSO-d₆), δ, ppm: 8.70 (br, 1H); 8.42(d, 1H); 7.91-7.64(m, 4H); 7.53-7.25(m, 7H); 5.26(d. 2H); 3.92(s, 3H); 3.97-3.76(m, 4H); 2.51-2.48(m, 2H); 1.25(d, 6H)

Example 4

2-(Pyridin-4-yl)-7-(4-methylpiperazin-1-yl)-9-benzylamino-10-cyano-s-triazolo[1,5-a]quinoline In the general formula (I) R¹ and R² stand for hydrogen atom, R³ stands for phenyl group, R⁵ stands for pyridin-4-yl group, R⁴ means group (b) where W stands for nitrogen atom, Z stands for —NR¹²-group where R¹² means methyl group, the value of m and o is 2, the value of r, p and t is 0, R¹³ stands for cyano group, X stands for NH group and the value of n is 1.

a.) 1,2-diamino-3-cyano-4-benzylamino-6-(4-amino-4-methylpiperazin-4-ium-1-yl)quinolinium ditosylate To the solution of 3.7 g of 2-amino-3-cyano-4-benzylamino-6-(4-methylpiperazin-1-yl)quinoline in 20 ml dimethylformamide, 4.4 g of O-tosylhydroxylamine in 50 ml dichloromethane is added dropwise at 20° C. in 15 minutes. After 5 hours of stirring the precipitated crystalline material is filtered off. After drying 3.3 g of the title compound is obtained (MH⁺: 404).

b.) 2-(pyridin-4-yl)-7-(4-methylpiperazin-1-yl)-9-benzylamino-10-cyano-s-triazolo[1,5-a]quinoline 3.2 g of 1,2-diamino-3-cyano-4-benzylamino-6-(4-amino-4-methylpiperazin-4-ium-1-yl)quinolinium ditosylate is dissolved in 50 ml ethanol and to this solution 20 ml of 1 mol/liter concentration sodium ethylate in ethanol solution and 2.1 g of pyridin-4-carbaldehyde are added. The reaction mixture is heated at reflux temperature for 4 hours. The precipitated crystalline material is filtered off and recrystallized from dimethylformamide. After drying 1.15 g of the title compound is obtained (MH⁺: 474).

¹H-NMR (DMSO-d₆), δ, ppm: 8.77 (br, 1H); 8.23(d, 1H); 8.12-7.64(m, 6H); 7.43-7.05(m, 5H); 5.13(d. 2H); 3.86(s, 3H); 3.46-3.34(m, 4H); 2.53-2.46(m, 4H); 2.28(s, 3H).

Example 4.2

2-(pyridin-4-yl)-7-(4-methylpiperazin-1-yl)-9-benzylamino-10-cyano-s-triazolo[1,5-a]quinoline maleate Title compound is prepared by the general method disclosed above by adding a solution of maleic acid to the compound prepared according to Example 4.

$^1$H-NMR (DMSO-d$_6$), δ, ppm: 8.78 (br, 1H); 8.24(d, 1H); 8.12-7.64(m, 6H); 7.43-7.05(m, 5H); 6.3(s, 2H); 5.15(d. 2H); 3.86(s, 3H); 3.46-3.34 (m, 4H); 2.51-2.46(m, 4H); 2.31(s, 3H).

Example 5

2-(4-methoxyphenyl)-7-(4-methylpiperazin-1-yl)-9-benzylamino-10-cyano-s-triazolo[1,5-a]quinoline In the general formula (I) R$^1$ and R$^2$ stand for hydrogen atom, R$^3$ stands for phenyl group, R$^5$ stands for 4-methoxyphenyl group, R$^4$ means group (b) where W stands for nitrogen atom, Z stands for —NR$^{12}$— group where R$^{12}$ means methyl group, the value of m and o is 2, the value of r, p and t is 0, R$^{13}$ stands for cyano group, X stands for NH group and the value of n is 1.

a.) 2-(4-methoxyphenyl)-7-(4-methylpiperazin-1-yl)-9-benzylamino-10-cyano-s-triazolo[1,5-a]quinoline 3.2 g of 1,2-diamino-3-cyano-4-benzylamino-6-(4-amino-4-methylpiperazin-4-ium-1-yl)quinolinium ditosylate, prepared according to Example 4, is dissolved in 50 ml ethanol, and to this solution 20 ml of 1 mol/liter concentration sodium ethylate in ethanol solution and 2 g of 4-methoxybenzaldehyde are added. The reaction mixture is heated at reflux temperature for 4 hours. The precipitated crystalline material is filtered off and recrystallized from dimethylformamide. After drying, 1.1 g of the title compound is obtained (MH$^+$: 504).

$^1$H-NMR (DMSO-d$_6$), δ, ppm: 8.65 (br, 1H); 8.21(d, 1H); 7.77-7.64(m, 4H); 7.43-7.05(m, 7H); 5.12(d. 2H); 3.81(s, 3H); 3.36-3.34(m, 4H); 2.53-2.49(m, 4H); 2.26(s, 3H).

Example 5.2

2-(4-methoxyphenyl)-7-(4-methylpiperazin-1-yl)-9-benzylamino-10-cyano-s-triazolo[1,5-a]quinoline-hemifumarate monohydrate Title compound is prepared by the general method disclosed above by adding a solution of fumaric acid to the compound prepared according to Example 5.

$^1$H-NMR (DMSO-d$_6$), δ, ppm: 8.68 (br, 1H); 8.23(d, 1H); 7.81-7.64(m, 4H); 7.53-7.05(m, 7H); 6.75 (s, 1H); 5.14(d, 2H); 3.84(s, 3H); 3.36-3.34 (m, 4H); 2.53-2.49(m, 4H); 2.33 (s, 3H).

Example 6

2-(3-methoxyphenyl)-7-(4-methylpiperazin-1-yl)-9-benzylamino-10-cyano-s-triazolo[1,5-a]quinoline In the general formula (I) R$^1$ and R$^2$ stand for hydrogen atom, R$^3$ stands for phenyl group, R$^5$ stands for 3-methoxyphenyl group, R$^4$ means group (b) where W stands for nitrogen atom, Z stands for —NR$^{12}$-group where R$^{12}$ means methyl group, the value of m and o is 2, the value of r, p and t is 0, R$^{13}$ stands for cyano group, X stands for NH group and the value of n is 1.

a.) 2-(3-methoxyphenyl)-7-(4-methylpiperazin-1-yl)-9-benzylamino-10-cyano-s-triazolo[1,5-a]quinoline 3.3 g of 1,2-diamino-3-cyano-4-benzylamino-6-(4-amino-4-methylpiperazin-4-ium-1-yl)quinolinium ditosylate, prepared according to Example 4, is dissolved in 50 ml ethanol, and to this solution 20 ml of 1 mol/l concentration sodium ethylate in ethanol solution and 2.1 g of 3-methoxybenzaldehyde are added. The reaction mixture is heated at reflux temperature for 4 hours. The precipitated crystalline material is filtered off and recrystallized from dimethylformamide. After drying, 1.15 g of the title compound is obtained (MH$^+$: 504).

$^1$H-NMR (DMSO-d$_6$), δ, ppm: 8.68 (br, 1H); 8.23(d, 1H); 7.79-7.64(m, 4H); 7.43-7.05(m, 7H); 5.12(d. 2H); 3.84(s, 3H); 3.36-3.34(m, 4H); 2.53-2.49(m, 4H); 2.26(s, 3H).

Example 6.2

2-(3-methoxyphenyl)-7-(4-methylpiperazin-1-yl)-9-benzylamino-10-cyano-s-triazolo[1,5-a]quinoline-hemifumarate hemihydrate Title compound is prepared by the general method disclosed above by adding a solution of fumaric acid to the compound prepared according to Example 6.

$^1$H-NMR (DMSO-d$_6$), δ, ppm: 8.68 (br, 1H); 8.23(d, 1H); 7.79-7.64(m, 4H); 7.43-7.05(m, 7H); 6.75 (s, 1H); 5.12(d, 2H); 3.84(s, 3H); 3.36-3.34 (m, 4H); 2.53-2.49(m, 4H); 2.31 (s, 3H).

Example 7

2-(3-hydroxyphenyl)-7-(4-methylpiperazin-1-yl)-9-benzylamino-10-cyano-s-triazolo[1,5-a]quinoline In the general formula (I) R$^1$ and R$^2$ stand for hydrogen atom, R$^3$ stands for phenyl group, R$^5$ stands for 3-hydroxyphenyl group, R$^4$ means group (b) where W stands for nitrogen atom, Z stands for —NR$^{12}$-group where R$^{12}$ means methyl group, the value of m and o is 2, the value of r, p and t is 0, R$^{13}$ stands for cyano group, X stands for NH group and the value of n is 1.

a.) 2-(3-hydroxyphenyl)-7-(4-methylpiperazin-1-yl)-9-benzylamino-10-cyano-s-triazolo[1,5-a]quinoline 3.1 g of 1,2-diamino-3-cyano-4-benzylamino-6-(4-amino-4-methylpiperazin-4-ium-1-yl)quinolinium ditosylate, prepared according to Example 4, is dissolved in 50 ml ethanol, and to this solution 20 ml of 1 mol/liter concentration sodium ethylate in ethanol solution and 2 g of 3-hydroxybenzaldehyde are added. The reaction mixture is heated at reflux temperature for 4 hours. The precipitated crystalline material is filtered off and recrystallized from dimethylformamide. After drying, 1.05 g of the title compound is obtained (MH$^+$: 490).

$^1$H-NMR (DMSO-d$_6$), δ, ppm: 9.61 (s, 1H); 8.68 (br, 1H); 8.23 (d, 1H); 7.79-7.64(m, 4H); 7.43-7.05(m, 7H); 5.12(d. 2H); 3.36-3.34(m, 4H); 2.53-2.49(m, 4H); 2.26(s, 3H).

Example 7.2

2-(3-hydroxyphenyl)-7-(4-methylpiperazin-1-yl)-9-benzylamino-10-cyano-s-triazolo[1,5-a]quinoline hydrochloride

Title compound is prepared by the general method disclosed above by adding a solution of hydrochloric acid to the compound prepared according to Example 7.

$^1$H-NMR (DMSO-d$_6$), δ, ppm: 9.61 (s, 1H); 8.78 (br, 1H); 8.26(d, 1H); 7.81-7.64(m, 4H); 7.48-7.05(m, 7H); 5.16(d. 2H); 3.46-3.34(m, 4H); 2.55-2.49(m, 4H); 2.36(s, 3H).

Example 8

2-(3-Methoxyphenyl)-7-(4-acetylpiperazin-1-yl)-9-benzylamino-10-cyano-s-triazolo[1,5-a]quinoline

In the general formula (I) R$^1$ and R$^2$ stand for hydrogen atom, R$^3$ stands for phenyl group, R$^5$ stands for 3-methoxyphenyl group, R$^4$ means group (b) where W stands for nitrogen atom, Z stands for —NR$^{12}$-group where R$^{12}$ means acetyl group, the value of m and o is 2, the value of r, p and t is 0, R$^{13}$ stands for cyano group, X stands for NH group and the value of n is 1.

a.) 2-Nitro-5-(piperazin-1-yl)benzoic acid

To the suspension of 50 g 2-nitro-5-chlorobenzoic acid in 750 ml water, 86 g of piperazine is added and the reaction mixture is heated at reflux temperature for 20 hours. The mixture is then neutralized with conc. hydrochloric acid and the precipitated crystalline material is filtered off and dried to obtain 62 g title compound (MH$^+$: 252)

b.) 2-nitro-5-(4-acetylpiperazin-1-yl)benzoic acid 30 g 2-nitro-5-(piparazin-1-yl)benzoic acid is added to 250 ml acetic anhydride and the mixture is stirred at 100° C. for 1 hour. The reaction mixture is diluted with 350 ml ice-water, the precipitated crystalline material is filtered off and dried to obtain 29 g title compound (MH$^+$: 294)

c.) 2-amino-5-(4-acetylpiperazin-1-yl)benzoic acid

The mixture of 7 g 2-nitro-5-(4-acetylpiparazin-1-yl)benzoic acid, 15 ml cyclohexene and 3 g Pd/C (10%) is heated in 120 ml ethyl alcohol at reflux temperature for 6 hours. The reaction mixture is filtered hot through a celit pad, the filtrate is evaporated to obtain 46.4 g title compound (MH$^+$: 264)

d.) 5-(4-acetylpiperazin-1-yl)isatoic anhydride

To the mixture of 18 g 2-amino-5-(4-acetylpiperazin-1-yl)benzoic acid and 60 ml dioxane, 10 ml diphosgene is added dropwise under stirring and cold water cooling. The mixture is then heated at reflux temperature for 2 hours. After cooling the solid material is filtered off, washed with 50 ml ether and dried. 24 g of the title compound is obtained (MH$^+$: 290).

e.) 2-Amino-3-cyano-4-hydroxy-6-(4-acetylpiperazin-1-yl)quinoline 4 g malononitrile is dissolved in 50 ml dimethylformamide and in several portions 2.4 g sodium hydride 60% dispersion is added to it. To the clear solution 8 g 5-(4-acetylpiperazin-1-yl)isatoic anhydride is added and the mixture is stirred at room temperature for 10 hours. The reaction mixture is diluted with 70 ml water and extracted with 2×30 ml ethyl acetate. The aqueous phase is evaporated to dryness at reduced pressure, the solid residue is dissolved in 20 ml water and the pH is adjusted to 6 with acetic acid. The precipitated material is filtered off and washed with water. After drying 6.5 g of the title compound is obtained (MH$^+$: 312).

f.) 2-Amino-3-cyano-4-chloro-6-(4-acetylpiperazin-1-yl)quinoline

The mixture of 1.7 g 2-amino-3-cyano-4-hydroxy-6-(4-acetylpiperazin-1-yl)quinoline, 50 ml acetonitrile and 3.4 ml phosphoryl chloride is heated at reflux temperature for 4 hours. The cooled reaction mixture is poured onto 30 g ice, the pH of the mixture is set to 8 with 10% sodium hydroxide solution and the resulting precipitate is filtered off. After drying 1.5 g of the title compound is obtained (MH$^+$: 330).

g.) 2-Amino-3-cyano-4-benzylamino-6-(4-acetylpiperazin-1-yl)quinoline 5 g 2-amino-3-cyano-4-chloro-6-(4-acetylpiperazin-1-yl) quinoline and 15 ml benzylamine is stirred at 125° C. for 1 h. The reaction mixture is then poured onto 30 ml water, the resulting precipitate is filtered off, washed with 20 ml water and dried to obtain 4 g of the title compound (MH$^+$: 401).

h.) 3-Methoxy-N-[6-(4-acetylpiperazin-1-yl)-4-benzylamino-3-cyanoquinolin-2-yl]benzamide To the solution of 1.2 g 2-amino-3-cyano-4-benzylamino-6-(4-acetylpiperazin-1-yl)quinoline in 20 ml pyridine, 1.5 g 3-methoxybenzoyl chloride is added and the mixture is heated at reflux temperature for 5 hours. The reaction mixture is poured onto 30 g ice-water and the precipitated solid material is filtered off. After drying 0.45 g of the title compound is obtained (MH$^+$: 535).

i) 1-Amino-2-(3-methoxybenzoylamino)-3-cyano-4-benzylamino-6-(4-acetylpiperazin-1-yl)quinolinium tosylate To the solution of 0.72 g 3-methoxy-N-[6-(4-acetylpiperazin-1-yl)-4-benzylamino-3-cyanoquinolin-2-yl]benzamide in 20 ml dimethylformamide, 0.6 g of O-tosylhydroxylamine in 25 ml dichloromethane is added dropwise at 20° C. in 15 minutes. After 5 hours of stirring the precipitated crystalline material is filtered off. After drying 0.65 g of the title compound is obtained (MH$^+$: 551).

j.) 2-(3-Methoxyphenyl)-7-(4-acetylpiperazin-1-yl)-9-benzylamino-10-cyano-s-triazolo[1,5-a]quinoline The solution of 0.7 g 1-amino-2-(3-methoxybenzoylamino)-3-cyano-4-benzylamino-6-(4-acetylpiperazin-1-yl) quinolinium tosylate, 5 ml pyridine and 0.3 ml DBU is heated at reflux temperature for 8 hours. The reaction mixture is poured onto 15 ml water and the precipitated solid material is filtered off. After drying 0.15 g title compound is obtained (MH$^+$: 532).

$^1$H-NMR (DMSO-d$_6$), δ, ppm: 8.68 (br, 1H); 8.33(d, 1H); 7.89-7.64(m, 4H); 7.53-7.05(m, 7H); 5.15(d. 2H); 3.82(s, 3H); 3.38-3.35(m, 4H); 2.63-2.59(m, 4H); 2.45(s, 3H).

Example 8.2

2-(3-Methoxyphenyl)-7-(4-acetylpiperazin-1-yl)-9-benzylamino-10-cyano-s-triazolo[1,5-a]quinoline hydrogensulfate Title compound is prepared by the general method disclosed above by adding a solution of sulphuric acid to the compound prepared according to Example 8.

$^1$H-NMR (DMSO-$d_6$), δ, ppm: 8.78 (br, 1H); 8.38(d, 1H); 7.91-7.64(m, 4H); 7.63-7.05(m, 7H); 5.17(d. 2H); 3.88(s, 3H); 3.68-3.45(m, 4H); 2.63-2.59(m, 4H); 2.48(s, 3H).

Example 9

2-(3-Methoxyphenyl)-7-(piperazin-1-yl)-9-benzylamino-10-cyano-s-triazolo[1,5-a]quinoline In the general formula (I) $R^1$ and $R^2$ stand for hydrogen atom, $R^3$ stands for phenyl group, $R^5$ stands for 3-methoxyphenyl group, $R^4$ means group (b), where W stands for nitrogen atom, Z stands for —$NR^{12}$-group where $R^{12}$ means hydrogen atom, the value of m and o is 2, the value of r, p and t is 0, $R^{13}$ stands for cyano group, X stands for NH group and the value of n is 1.

a.) 2-(3-methoxyphenyl)-7-(piperazin-1-yl)-9-benzylamino-10-cyano-s-triazolo[1,5-a]quinoline 0.24 g of 2-(3-methoxyphenyl)-7-(4-acetylpiperazin-1-yl)-9-benzylamino-10-cyano-s-triazolo[1,5-a]quinoline in 8 ml 3 N concentration hydrochloric acid solution is heated at reflux temperature for 6 hours. The reaction mixture is neutralized with 10% sodium hydroxide solution and the precipitated solid material is filtered off. After drying 0.1 g title compound is obtained (MH$^+$: 490).

$^1$H-NMR (DMSO-$d_6$), δ, ppm: 8.68 (br, 1H); 8.33(d, 1H); 8.11(br, 1H); 7.89-7.64(m, 4H); 7.53-7.05(m, 7H); 5.15(d. 2H); 3.82(s, 3H); 3.38-3.35(m, 4H); 2.63-2.59(m, 4H).

Example 9.2

2-(3-methoxyphenyl)-7-(piperazin-1-yl)-9-benzylamino-10-cyano-s-triazolo[1,5-a]quinoline maleate Title compound is prepared by the general method disclosed above by adding a solution of maleic acid to the compound prepared according to Example 9.

$^1$H-NMR (DMSO-$d_6$), δ, ppm: 8.68 (br, 1H); 8.33(d, 1H); 8.02(br, 1H); 7.89-7.64(m, 4H); 7.53-7.05(m, 7H); 6.32(s, 2H); 5.13(d. 2H); 3.82(s, 3H); 3.38-3.35(m, 4H); 2.63-2.59 (m, 4H).

Example 10

2-Phenyl-7-(pyridin-3-yl)-9-benzylamino-10-cyano-s-triazolo[1,5-a]quinoline In the general formula (I) $R^1$ and $R^2$ stand for hydrogen atom, $R^3$ stands for phenyl group, $R^4$ stands for pyridin-3-yl group $R^5$ stands for phenyl group, $R^{13}$ stands for cyano group, X stands for NH group and the value of n is 1.

a.) 1,2-Diamino-3-cyano-4-hydroxy-6-iodoquinolinium tosylate 0.62 g of 2-amino-3-cyano-4-hydroxy-6-iodoquinoline is stirred for 40 minutes in 10 ml dimethylformamide in the presence of 1 g solid potassium carbonate, then the solution of 0.6 g O-tosyl-hydroxylamine in 14 ml dichloromethane is added dropwise. After stirring the reaction mixture at room temperature for 4 hours, the precipitated solid material is filtered off and dried to obtain 0.57 g of the title compound (MH$^+$: 327).

b.) 2-Phenyl-7-iodo-9-hydroxy-10-cyano-s-triazolo[1,5-a]quinoline 0.32 g of 1,2-diamino-3-cyano-4-hydroxy-6-iodoquinolinium tosylate is dissolved in 15 ml ethanol and to this solution 2 ml of 1 mol/liter concentration sodium ethylate in ethanol solution and 0.16 g of benzaldehyde is added. The reaction mixture is heated at reflux temperature for 1 hour. The precipitated crystalline material is filtered off and washed with ethanol and water. After drying 0.34 g of the title compound is obtained (MH$^+$: 413).

c.) 2-Phenyl-7-iodo-9-chloro-10-cyano-s-triazolo[1,5-a]quinoline

To the solution of 5 g 2-phenyl-7-iodo-9-hydroxy-10-cyano-s-triazolo[1,5-a]quinoline in 50 ml of acetonitrile, 9 g phosphoryl chloride is added and the mixture is heated at reflux temperature for 5 hours. The reaction mixture is poured onto 500 ml ice-water, the solid material is filtered off and dried to obtain 5 g of the title compound (MH$^+$: 431).

d.) 2-phenyl-7-iodo-9-benzylamino-10-cyano-s-triazolo[1,5-a]quinoline 2.5 g of 2-phenyl-7-iodo-9-chloro-10-cyano-s-triazolo[1,5-a]quinoline and 10 g of benzylamine are mixed and stirred at room temperature for 15 minutes. The reaction mixture is diluted with diethyl ether—hexane mixture and the precipitated solid material is filtered off. After drying 1.88 g of the title compound is obtained (MH$^+$: 562).

e.) 2-phenyl-7-(pyridin-3-yl)-9-benzylamino-10-cyano-s-triazolo[1,5-a] quinoline To the suspension of 0.6 g 2-phenyl-7-iodo-9-benzylamino-10-cyano-s-triazolo[1,5-α]quinoline in 10 ml dimethoxyethane, 0.1 g of tetrakis(triphenylphosphine)palladium(0), 0.25 g of pyridine-3-boronic acid and 10 ml of 1 mol/liter concentration sodium hydrogen carbonate solution are added. The reaction mixture is stirred under argon atmosphere at reflux temperature for 5 hours, then it is evaporated and the residue is treated with ethyl acetate. The precipitated solid material is filtered off. After drying 0.3 g of the title compound is obtained (MH$^+$: 453).

The above compound can also be prepared in the following way:

f) 2-Phenyl-7-trimethylstannyl-9-benzylamino-10-cyano-s-triazolo[1,5-a]quinoline The solution of 0.25 g 2-phenyl-7-iodo-9-benzylamino-10-cyano-s-triazolo[1,5-α]quinoline, 0.6 g hexamethyldistannate and 0.1 g tetrakis(triphenylphosphine)palladium(0) in 3 ml dioxane is heated at reflux temperature under nitrogen atmosphere for 5 hours. The solvent is then removed and the residue is treated with diethyl ether. The precipitated solid material is filtered off. After drying, 0.24 g title compound is obtained (M$^+$: 539).

g.) 2-Phenyl-7-(pyridin-3-yl)-9-benzylamino-10-cyano-s-triazolo[1,5-α] quinoline To the solution of 0.2 g 2-phenyl-7-trimethylstannyl-9-benzylamino-10-cyano-s-triazolo[1,5-α]quinoline in 10 ml dimethylformamide, 0.05 g of tetrakistriphenylpalladium(0) and 0.1 g of 3-bromopyridine are added. The solution is stirred at 100° C. under nitrogen atmosphere. The solvent is then removed at reduced pressure and the residue is treated with ethyl acetate. The precipitated solid material is filtered off. After drying 0.1 g title compound is obtained (MH$^+$: 453).
$^1$H-NMR (DMSO-d$_6$), δ, ppm: 8.68 (br, 1H); 8.33(d, 1H); 8.12-7.91(m, 4H); 7.89-7.64(m, 5H); 7.53-7.05(m, 7H); 5.15 (d, 2H).

Example 10.2

2-Phenyl-7-(pyridin-3-yl)-9-benzylamino-10-cyano-s-triazolo[1,5-α]quinoline hydrogensulfate Title compound is prepared by the general method disclosed above by adding a solution of sulphuric acid to the compound prepared according to Example 10.
$^1$H-NMR (DMSO-d$_6$), δ, ppm: 8.78 (br, 1H); 8.43(d, 1H); 8.32-7.96(m, 4H); 7.89-7.74(m, 5H); 7.53-7.05(m, 7H); 5.17 (d, 2H).

Example 11

2-Phenyl-7-(4-methylpiperazin-1-yl)-9-(2-pyridylmethylamino)-10-cyano-s-triazolo[1,5-α]quinoline In the general formula (I) R$^1$ and R$^2$ stand for hydrogen atom, R$^3$ stands for pyridin-2-yl group, R$^4$ means group (b), where W stands for nitrogen atom, Z stands for —NR$^{12}$- group where R$^{12}$ means methyl group, the value of m and o is 2, the value of r, p and t is 0, R$^5$ stands for phenyl group, R$^{13}$ stands for cyano group, X stands for NH group and the value of n is 1.

a.) 1,2-Diamino-3-cyano-4-hydroxy-6-(4-amino-4-methylpiperazin-4-ium-1-yl)quinolinium ditosylate To the solution of 3.7 g of 2-amino-3-cyano-4-hydroxy-6-(4-methylpiperazin-1-yl)quinoline in 20 ml dimethylformamide, 4.4 g of O-tosylhydroxylamine in 50 ml dichloromethane is added dropwise at 20° C. in 15 minutes. After 5 hours of stirring the precipitated crystalline material is filtered off and dried to obtain 3.1 g of the title compound (MH$^+$: 315).

b.) 2-Phenyl-7-(4-methylpiperazin-1-yl)-9-hydroxy-10-cyano-s-triazolo[1,5-α]quinoline 3.1 g of 1,2-diamino-3-cyano-4-hydroxy-6-(4-amino-4-methylpiperazin-4-ium-1-yl)quinolinium ditosylate is dissolved in 50 ml ethanol and to this solution 20 ml of 1 mol/liter concentration sodium ethylate in ethanol and 2 g of benzaldehyde are added. The reaction mixture is heated at reflux temperature for 4 hours. The precipitated crystalline material is filtered off and recrystallized from dimethylformamide. After drying 1.15 g of the title compound is obtained (MH$^+$: 385).

c.) 2-Phenyl-7-(4-methylpiperazin-1-yl)-9-chloro-10-cyano-s-triazolo[1,5-α]quinoline The mixture of 1.5 g 2-phenyl-7-(4-methylpiperazin-1-yl)-9-hydroxy-10-cyano-s-triazolo[1,5-α]quinoline and 3.4 ml phosphoryl chloride is heated at 120° C. for 4 hours. The cooled reaction mixture is poured onto 30 g of ice, the pH of the mixture is set to 8 with 10% sodium hydroxide solution and the resulting precipitate is filtered off. After drying, 1.3 g of the title compound is obtained (MH$^+$: 403).

d.) 2-phenyl-7-(4-methylpiperazin-1-yl)-9-(2-pyridylmethylamino)-10-cyano-s-triazolo[1,5-α]quinoline 1 g of 2-phenyl-7-(4-methylpiperazin-1-yl)-9-chloro-10-cyano-s-triazolo[1,5-α]quinoline in 5 ml 2-(aminomethyl)pyridine is stirred at room temperature for 2 hours, then the reaction mixture is diluted with 20 ml of water and the precipitated solid material is filtered off. After drying, 1.1 g of the title compound is obtained (MH$^+$: 475).
$^1$H-NMR (DMSO-d$_6$), δ, ppm: 8.68 (br, 1H); 8.33(d, 1H); 8.19-7.64(m, 4H); 7.53-7.05(m, 7H); 5.15(d. 2H); 3.38-3.35 (m, 4H); 2.63-2.59(m, 4H); 2.26(s, 3H).

Example 11.2

2-phenyl-7-(4-methylpiperazin-1-yl)-9-(2-pyridylmethylamino)-10-cyano-s-triazolo[1,5-α]quinoline hydrochloride Title compound is prepared by the general method disclosed above by adding a solution of hydrochloric acid to the compound prepared according to Example 11.
$^1$H-NMR (DMSO-d$_6$), δ, ppm: 8.78 (br, 1H); 8.43(d, 1H); 8.29-7.64(m, 4H); 7.53-7.05(m, 7H); 5.15(d. 2H); 3.38-3.35 (m, 4H); 2.73-2.59(m, 4H); 2.36(s, 3H).

Example 12

2-(3-Methoxyphenyl)-7-(pyridin-3-yl)-9-(4-pyridylmethlamino)-10-cyano-s-triazolo[1,5-α]quinoline In the general formula (I) R$^1$ and R$^2$ stand for hydrogen atom, R$^3$ stands for pyridin-4-yl group, R$^4$ stands for pyridin-3-yl group, R$^5$ stands for 3-methoxyphenyl group, R$^{13}$ stands for cyano group, X stands for NH group and the value of n is 1.

a.) 1,2-Diamino-3-cyano-4-hydroxy-6-iodo-quinolinium tosylate 0.62 g 2-amino-3-cyano-4-hydroxy-6-iodoquinoline in 10 ml of dimethylformamide is stirred with 1 g of solid potassium carbonate for 40 minutes. Then, 0.6 g O-tosylhydroxylamine in 14 ml dichloromethane is added dropwise to the reaction mixture. Stirring at room temperature is continued for 4 hours. The precipitated crystalline material is filtered off and dried to obtain 0.57 g of the title compound (MH+: 327).

b.) 2-(3-Methoxyphenyl)-7-iodo-9-hydroxy-10-cyano-s-triazolo[1,5-a]quinoline 0.32 g of 1,2-diamino-3-cyano-4-hydroxy-6-iodoquinolinium tosylate, prepared in Example 10, is dissolved in 15 ml ethanol and to this solution 2 ml of 1 mol/liter concentration sodium ethylate in ethanol solution and 0.16 g of 3-methoxybenzaldehyde are added. The reaction mixture is heated at reflux temperature for 1 hour. The precipitated solid material is filtered off and washed with ethanol and water. After drying, 0.33 g of the title compound is obtained (MH+: 442).

c.) 2-(3-methoxyphenyl)-7-iodo-9-chloro-10-cyano-s-triazolo[1,5-α]quinoline

To the solution of 5 g 2-(3-methoxyphenyl)-7-iodo-9-hydroxy-10-cyano-s-triazolo[1,5-α]quinoline in 50 ml of acetonitrile, 9 g phosphoryl chloride is added and the mixture is heated at reflux temperature for 5 hours. The reaction mixture is poured onto 500 ml ice-water, the precipitate is filtered off and dried to obtain 5 g of the title compound (MH+: 461).

d.) 2-(3-Methoxyphenyl)-7-iodo-9-(4-pyridylmethylamino)-10-cyano-s-triazolo[1,5-α]quinoline 2.5 g of 2-(3-methoxyphenyl)-7-iodo-9-chloro-10-cyano-s-triazolo[1,5-a]quinoline and 10 g of (4-pyridyl)methylamine are mixed and stirred at room temperature for 15 minutes. The reaction mixture is diluted with diethyl ether/hexane mixture and the precipitated solid material is filtered off. After drying, 1.88 g of the title compound is obtained (MH+: 533).

e.) 2-(3-Methoxyphenyl)-7-(pyridin-3-yl)-9-(4-pyridylmethylamino)-10-cyano-s-triazolo[1,5-α]quinoline To the suspension of 0.6 g 2-(3-methoxyphenyl)-7-iodo-9-(4-pyridylmethylamino)-10-cyano-s-triazolo[1,5-α]quinoline in 10 ml dimethoxyethane, 0.1 g of tetrakistriphenylpalladium(0), 0.25 g of pyridine-3-boronic acid and 10 ml of 1 mol/liter concentration sodium hydrogen carbonate solution are added. The reaction mixture is stirred under argon atmosphere at reflux temperature for 5 hours, then it is evaporated and the residue is treated with ethyl acetate. The precipitated solid material is filtered off. After drying 0.35 g of the title compound is obtained (MH+: 484).

$^1$H-NMR (DMSO-$d_6$), δ, ppm: 8.68 (br, 1H); 8.33(d, 1H); 8.29-7.84(m, 4H); 7.79-7.64(m, 3H); 7.53-7.05(m, 7H); 5.18 (d. 2H); 3.84(s, 3H).

Example 12.2

2-(3-Methoxyphenyl)-7-(pyridin-3-yl)-9-(4-pyridylmethylamino)-10-cyano-s-triazolo[1,5-α]quinoline hydrogensulfate Title compound is prepared by the general method disclosed above by adding a solution of sulphuric acid to the compound prepared according to Example 12.

$^1$H-NMR (DMSO-$d_6$), δ, ppm: 8.78 (br, 1H); 8.38(d, 1H); 8.36-7.89(m, 4H); 7.79-7.69(m, 3H); 7.63-7.05(m, 7H); 5.18 (d. 2H); 3.91 (s, 3H).

By the above procedures, using the appropriate starting materials, the following compounds of the general formula (I) shown in Table 1. have been prepared:

TABLE 1

(General structure: quinoline-triazolo scaffold with substituents $R^3$, $R^4$, $R^5$ and a CN group; $R^3$ attached via HN-CH$_2$-)

| Example | R3 | R4 | R5 | MH+ LC-MS |
|---|---|---|---|---|
| 13. | phenyl | 4-methylpiperazin-1-yl (via methyl linker) | pyridin-3-yl | 475 |
| 14. | phenyl | 4-methylpiperazin-1-yl (via methyl linker) | pyridin-2-yl | 475 |
| 15. | phenyl | 4-methylpiperazin-1-yl (via methyl linker) | 4-hydroxyphenyl | 490 |
| 16. | phenyl | 4-methylpiperazin-1-yl (via methyl linker) | 2-fluorophenyl | 492 |
| 17. | phenyl | 4-methylpiperazin-1-yl (via methyl linker) | phenyl | 474 |
| 18. | phenyl | 4-methylpiperazin-1-yl (via methyl linker) | 4-fluorophenyl | 492 |
| 19. | phenyl | piperazin-1-yl (via methyl linker) | phenyl | 460 |

TABLE 1-continued

| Example | R3 | R4 | R5 | MH+ LC-MS |
|---|---|---|---|---|
| 20. | phenyl | 4-benzyl-piperazin-1-yl | 3-methoxyphenyl | 580 |
| 21. | phenyl | pyridin-3-yl | 3-methoxyphenyl | 483 |
| 22. | phenyl | pyridin-4-yl | 3-methoxyphenyl | 483 |
| 23. | phenyl | pyridin-4-yl | phenyl | 453 |
| 24. | phenyl | morpholin-4-yl | 3-hydroxyphenyl | 477 |
| 25. | phenyl | morpholin-4-yl | phenyl | 461 |
| 26. | phenyl | morpholin-4-yl | thiazol-2-yl | 468 |
| 27. | phenyl | (2R,6S)-2,6-dimethylmorpholin-4-yl | phenyl | 489 |
| 28. | phenyl | (2R,6S)-2,6-dimethylmorpholin-4-yl | 3-methoxyphenyl | 519 |
| 29. | pyridin-3-yl | 4-methylpiperazin-1-yl | phenyl | 475 |
| 30. | pyridin-2-yl | 4-methylpiperazin-1-yl | 3-methoxyphenyl | 505 |
| 31. | pyridin-3-yl | 4-methylpiperazin-1-yl | 3-methoxyphenyl | 505 |
| 32. | pyridin-3-yl | pyridin-3-yl | phenyl | 454 |
| 33. | pyridin-3-yl | pyridin-3-yl | 3-methoxyphenyl | 484 |
| 34. | pyridin-2-yl | pyridin-3-yl | 3-methoxyphenyl | 484 |
| 35. | phenyl | dimethylamino | 3-methoxyphenyl | 449 |

TABLE 1-continued

| Example | R3 | R4 | R5 | MH+ LC-MS |
|---|---|---|---|---|
| 36 | phenyl | -N(CH3)2 | 4-methoxyphenyl | 449 |
| 37 | phenyl | -N(CH2CH3)2 | 3-methoxyphenyl | 477 |
| 38 | phenyl | -N(CH2CH3)2 | 4-methoxyphenyl | 477 |

Example 39

By known methods the tablets of the following composition are prepared:

| | |
|---|---|
| Active ingredient | 25 mg |
| Lactose | 50 mg |
| Avicel | 21 mg |
| Crospovidone | 3 mg |
| Magnesium stearate | 1 mg |

Biology
Methods
Human Adenosine $A_3$ Receptor Binding

Preparing membrane suspension: ovarium cells of cloned golden hamster expressing human $A_3$ receptor (further: CHO-h$A_3$) are appropriately cultured. Achieving confluent cell layer, the cultivating liquid is removed from the cells by washing them with 37° C. PBS, then the cell are suspended in ice cold PBS, washed 3 times with PBS, centrifuged (1000×g 10 minutes) (Sigma 3K30) and homogenated using teflon homogenizer (B. Braun Potter S) at 1500/min rotation speed, for 15 sec. in the following buffer: 50 mM Tris, 10 mM MgCl$_2$, 1 mM EDTA, pH 8.0. The homogenate is centrifuged (43.000 g, 10 min). The precipitate is suspended in the above buffer, protein concentration 0.1 mg/ml (Bradford method). Aliquots of the membrane preparatum are store at −80° C. hA3-CHO membrane preparation from Perkin Elmer was used alternatively.

Binding protocol: incubate CHO-h$A_3$ membrane preparation (2 µg protein content) in the presence of the test material and 0.5 nM [$^{125}$I]AB-MECA (4-amino-3-iodo-benzyl-5'-N-methylcarboxamide-adenosine) (100.000 cpm) in incubation buffer (50 mM Tris, 10 mM MgCl$_2$, 1 mM EDTA, 3 U/mL adenosine deaminase, pH 8.0). Define the non-specific radioligand binding in the presence of 100 µM R-PIA (N$^6$[L-2-phenylisopropyl]adenosine). Total volume of the reaction is 50 µL for 60 min at room temperature. Filter the reaction mixture over Whatman GF/B glass fibre filters (pre-soaked in 0.5% polyethylenimine for 3 hours) under 25 Hgmm vacuum, wash 4× with 1 mL ice-cold washing buffer (50 mM Tris, 10 mM MgCl$_2$, 1 mM EDTA, pH 8.0), on a 96-well Brandel Cell Harvester. Detect the radioactivity in gamma-counter (1470 Wizard, Wallac). Inhibition [%]=100−((activity in the presence of test compound−non-specific activity)/(total activity−non-specific activity))*100

Human Adenosine $A_1$ Receptor Binding

Binding protocol: incubate membrane preparate of human A1 adenosine receptor expressing CHO cells (protein content: 10 µg), (source: Perkin-Elmer), in the presence of the test material and 10 nM [$^3$H]DPCPX (8-cyclopenthyl-1,3-dipropylxanthine) (200.000 dpm) in incubation buffer (50 mM Tris HCl, pH 7.4, 3 U/mL adenosine deaminase). Define the non-specific radioligand binding in the presence of 10 µM R-PIA (N$^6$-[IL-2-phenylisopropyl]adenosine) Total volume of the reaction: 100 µL, for 3 hr at room temperature. Filter the reaction mixture over Whatman GF/B glass fibre filters (pre-soaked in 0.5% polyethylimine for 3 hours) under 25 Hgmm vacuum, wash 4× with 1 mL ice-cold washing buffer (50 mM Tris HCl, pH 7.4) on a 96-well Brandel Cell Harvester. Detect the radioactivity in beta-counter (1450 Microbeta, Wallac), in the presence of 200 µL HiSafe-3 cocktail. Inhibition [%]=100−((activity in the presence of test compound−non-specific activity)/(total activity−non-specific activity))*100

Human Adenosine $A_{2a}$ Receptor Binding

Binding protocol: Incubate membrane preparatum of human $A_{2a}$ adenosine receptor expressing HEK-293 cells (10 µg protein content), (source: Perkin-Elmer, in the presence of the test material and 20 nM [$^3$H]CGS-21680 (2-[p-(2-carbonylethyl)phenylethylamino]-5'-N-ethylcarboxamido-adenosine) (200.000 dpm) in incubation buffer (50 mM Tris-HCl, 10 mM MgCl$_2$, 1 mM EDTA, 2 U/mL adenosine deaminase, pH 7.4).

Define the non-specific binding in the presence of 50 µM NECA (5'-N-ethylcarboxamido-adenosine). Total volume of the reaction: 100 µl for 90 min at room temperature. Filter the reaction mixture under 25 Hgmm vacuum over Whatman GF/B glass fibre filter (pre-soaked for 3 hours in 0.5% polyethylimine), wash 4× with 1 mL ice-cold washing buffer (50 mM Tris HCl, 10 mM MgCl$_2$, 1 mM EDTA, 0.9% NaCl, pH 7.4) on 96-well Brandel Cell Harvester. Detect the radioactivity in beta-counter (1450 Microbeta, Wallac) in the presence of 200 µL HiSafe-3 cocktail. Inhibition [%]=100−((activity in the presence of test compound−non-specific activity)/(total activity−non-specific activity))*100.

Human Adenosine $A_{2b}$ Receptor Binding

Binding protocol: incubate membrane preparate of human $A_{2b}$ adenosine receptor expressing HEK-293 cells (protein content: 10 µg), (source: Perkin-Elmer), in the presence of the test material and 32.4 nM [$^3$H]DPCPX (8-cyclopenthyl-1,3-dipropylxanthine) (800.000 dpm) in incubation buffer (50 mM Tris-HCl, 10 mM MgCl$_2$, 1 mM EDTA, 0.1 mM benzamidine, 2 U/mL adenosine deaminase, pH 6.5). Define the non-specific radioligand binding in the presence of 100 μM NECA (5'-N-ethylcarboxamido-adenosine). Total volume of the reaction mixture: 100 μL for 30 min at room temperature. Filter the reaction mixture under 25 Hgmm vacuum over Whatman GF/C glass fibre filter (pre-soaked in 0.5% polyethylimine for 3 hours), wash 4× with 1 mL ice-cold washing buffer (50 mM Tris-HCl, pH 6.5) on 96-well Brandel Cell Harvester. Detect the radioactivity: in beta-counter (1450 Microbeta, Wallac) in the presence of 200 μL of HiSafe-3 cocktail Inhibition [%]=100−((activity in the presence of test compound−non-specific activity)/(total activity−non-specific activity))*100.

Allergic Mouse Model

Male BalbC mice of 20-25 g body weight are used for the experiments. The animals are first allergized with ovalbumin, then three weeks after the first ovalbumin injection they are involved into the experiment. On the day of the experiment the mice are treated (per os) with the experimental material (or with the vehicle containing no active ingredient), then after a suitable waiting period they are narcotized. After surgical opening of the trachea, 10 microliter of 1% ovalbumin solution is injected into the trachea.

The control group receives vehicle (physiological salt solution) into the trachea. After surgical closing of the trachea and treatment of the wound, the animals are separated and kept under their usual life conditions for 24 h.

After 24 hours the animals are over narcotized, the trachea is opened again and the lung is washed with buffer solution. The buffer solution is centrifuged, the cell sediment is resuspended again, and then the cells are counted. The total cell number is determined and the different leukocytes are sorted on the bases of the morphology. To determine the effectivity of the experimental material, the inhibition % is calculated in comparison to the control group. To determine the significance of the effect, statistical evaluation is carried out.

Biological Results:

We consider a compound biologically active if at a concentration of 1 μM, under the above experimental conditions, it inhibits the binding of the radioligand to the human adenosine $A_3$ receptors with an activity higher than 80%.

Based on the radioisotope saturation curves using Scatchard analysis (G. Scatchard, Ann. N.Y. Acad. Sci. 51:660, 1949) the dissociation constant ($K_d$) of the radioligand [$^{125}$I] AB-MECA on the CHO-hA$_3$ membrane preparate is determined. From the $K_d$ values, applying the Cheng-Prusoff equation (Y. J. Cheng and W. H. Prusoff, Biochem. Pharmacol. 22:3099, 1973) the affinity constants ($K_i$) of the test compounds are calculated from their IC$_{50}$ values.

The compounds of the general formula (I) display in general an IC$_{50}$ value of less than 500 nM. The favourable compounds, shown by the examples, possess an IC$_{50}$ value of less than 100 nM. The most active compounds of the general formula (I) possess an IC$_{50}$ value in the range of 1 nM to 20 nM.

The compounds of the general formula (I) have good bioavailability and are selectivite compared to the human adenosine $A_1$, $A_{2a}$ and $A_{2b}$ receptor subtypes.

The in vivo studies the compounds of the general formula (I) according to the invention revealed that they are very active inhibitors of the inflammation processes occurring in asthma.

Furthermore, the duration of action of the compounds of the general formula (I) following intravenous and oral administration is long, their ID$_{50}$ values are low and their toxicological and side-effect profiles are advantageous.

As an example, the values of the adenosine $A_3$ receptor binding, the solubility and the anti-inflammatory activity of the compounds of the general formula (I) described in examples 1, 17 and 18 are demonstrated as follows:

| Example: | IC$_{50}$ [nM] | Solubility[mg/l] pH: 1; 6.5; 7.5 | Inhibition of cell migration [%]* |
|---|---|---|---|
| 1. | 38 | 500; 0.2; 2 | 81 |
| 17. | 7.7 | 3000; 0.5; 5 | 88 |
| 18. | 11 | 2500; 0.5; 13 | 57 |

*Ovalbumin induced cell migration, % inhibition (full), p.o. mice 24 h, 10 mg/kg CMC.

The above data are showing that the compounds of the general formula (I) according to the invention are potential outstanding therapeutic agents.

The invention claimed is:
1. A compound of the general formula (I),

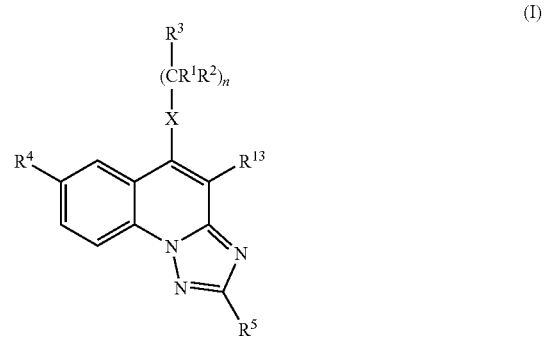

wherein
R$^1$ stands for hydrogen atom or for straight or branched C$_{1-4}$ alkyl group;
R$^2$ stands for hydrogen atom or for straight or branched C$_{1-4}$ alkyl group;
R$^3$ stands for hydrogen atom or for straight or branched C$_{1-4}$ alkyl group, or C$_{3-6}$ cycloalkyl group, or
a phenyl- or thienyl-, or furyl group, optionally substituted with one or more, identical or different, straight or branched C$_{1-4}$ alkyl group, straight or branched C$_{1-4}$ alkoxy group, hydroxyl group or halogen atom, or
a 5- or 6-membered heterocyclic ring containing one or two or three nitrogen atoms, or a 5-membered heterocyclic ring containing one nitrogen atom and one oxygen atom, or one nitrogen atom and one sulphur atom, optionally substituted with one or more, identical or different, straight or branched C$_{1-4}$ alkyl group, straight or branched C$_{1-4}$ alkoxy group, hydroxyl group or halogen atom;
R$^4$ stands for a phenyl-, benzyl-, thienyl-, or furyl group, optionally substituted with methylenedioxy group, or with one or more, identical or different, straight or branched C$_{1-4}$ alkyl group, straight or branched C$_{1-4}$ alkoxy group, hydroxyl group, trifluoromethyl group, cyano group, or halogen atom, or
a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched C$_{1-4}$ alkyl group, straight or branched $C_{1-4}$ alkoxy group, or halogen atom, or a group of the general formula (a),

(a)

wherein
  $R^6$ and $R^7$ independently stand for hydrogen atom, $C_{3-6}$ cycloalkyl group, benzyl group, or a straight or branched $C_{14}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or
a group of the general formula (b),

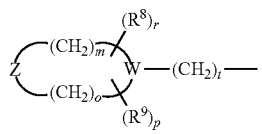
(b)

wherein
  $R^8$ and $R^9$ independently stand for straight or branched $C_{1-4}$ alkyl group, $C_{3-6}$ cycloalkyl group or hydroxyl group;
  Z means oxygen atom, sulphur atom, —$CHR^{11}$- group or —$NR^{12}$ group, where $R^{11}$ and $R^{12}$ independently stand for hydrogen atom, straight or branched $C_{1-4}$ alkyl group, $C_{3-6}$ cycloalkyl group, benzyl group, or —$CH_2$—$(C_{1-5}$ straight or branched acyl)-group, —$CH_2$—$CH_2O$—$(C_{1-4}$ straight or branched alkyl)-group or $C_{1-5}$ straight or branched acyl group;
  W means nitrogen atom or —CH-group;
  m is a value of 1, 2 or 3;
  o is a value of 1, 2 or 3;
  p is a value of zero or 1;
  r is a value of zero or 1;
  t is a value of zero or 1;
$R^5$ stands for hydrogen atom, straight or branched $C_{1-4}$ alkyl group, or
  a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
  a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, hydroxyl group or halogen atom;
$R^{13}$ stands for cyano group, aminocarbonyl group, —CO—O—$(C_{1-4}$ straight or branched alkyl) group or carboxyl group;
X means —$CH_2$— group, —NH— group, —$NR^{10}$— group, or sulphur atom, or oxygen atom, or —SO— or —$SO_2$— group, where $R^{10}$ stands for straight or branched $C_{1-4}$ alkyl group or $C_{3-6}$ cycloalkyl group; and
n is a value of zero, 1 or 2;
and the salts and N-oxides thereof.

2. A compound according to claim 1,
wherein
$R^1$ stands for hydrogen atom or for straight or branched $C_{1-4}$ alkyl group;
$R^2$ stands for hydrogen atom or for straight or branched $C_{1-4}$ alkyl group;
$R^3$ stands for hydrogen atom or for straight or branched $C_{1-4}$ alkyl group, or $C_{3-6}$ cycloalkyl group, or
  a phenyl- or thienyl-, or furyl group, optionally substituted with one or more, identical or different, straight or branched $C_{1-4}$ alkyl group, straight or branched alkoxy group, or halogen atom, or
  a 5- or 6-membered heterocyclic ring containing one or two or three nitrogen atoms, or a 5-membered heterocyclic ring containing one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;
$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
  a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or
  a group of the general formula (a), wherein
    $R^6$ and $R^7$ independently stand for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or
  a group of the general formula (b), wherein
    $R^8$ and $R^9$ independently stand for straight or branched $C_{1-4}$ alkyl group or $C_{3-6}$ cycloalkyl group;
    Z means oxygen atom, sulphur atom, —$CHR^{11}$— group or —$NR^{12}$— group, where $R^{11}$ and $R^{12}$ independently stand for hydrogen atom, straight or branched $C_{1-4}$ alkyl group, $C_{3-6}$ cycloalkyl group, benzyl group, or —$CH_2$—$(C_{1-5}$ straight or branched acyl)- group, —$CH_2$—$CH_2$—O—$(C_{1-4}$ straight or branched alkyl)- group or $C_{1-5}$ straight or branched acyl group;
    W means nitrogen atom or —CH— group;
    m is a value of 1, 2 or 3;
    o is a value of 1, 2 or 3;
    p is a value of zero or 1;
    r is a value of zero or 1;
    t is a value of zero or 1;
$R^5$ stands for hydrogen atom, straight or branched $C_{1-4}$ alkyl group, or
  a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group, aminocarbonyl group, —CO—O—($C_{1-4}$ straight or branched alkyl) group or carboxyl group;

X means —$CH_2$— group, —NH— group, —$NR^{10}$— group, or sulphur atom, or oxygen atom, or —SO— or —$SO_2$— group, where $R^{10}$ stands for straight or branched $C_{1-4}$ alkyl group or $C_{3-6}$ cycloalkyl group; and n is a value of zero, 1 or 2;

and the salts and N-oxides thereof.

3. A compound according to claim 1, wherein $R^1$ stands for hydrogen atom or for straight or branched $C_{1-4}$ alkyl group;

$R^2$ stands for hydrogen atom or for straight or branched $C_{1-4}$ alkyl group;

$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or a 5- or 6-membered heterocyclic ring containing one or two or three nitrogen atoms, or a 5-membered heterocyclic ring containing one nitrogen atom and one oxygen atom or one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a), wherein $R^6$ and $R^7$ independently stand for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein $R^8$ and $R^9$ independently stand for straight or branched $C_{1-4}$ alkyl group or $C_{3-6}$ cycloalkyl group;

Z means oxygen atom, sulphur atom, —$CHR^{11}$— group or —$NR^{12}$— group, where $R^{11}$ and $R^{12}$ independently stand for hydrogen atom, straight or branched $C_{1-4}$ alkyl group, $C_{3-6}$ cycloalkyl group, benzyl group, or —$CH_2$—($C_{1-5}$ straight or branched acyl)-group, —$CH_2$—$CH_2$—O—($C_{1-4}$ straight or branched alkyl)-group or $C_{1-5}$ straight or branched acyl group;

W means nitrogen atom or —CH— group;

m is a value of 1, 2 or 3;

o is a value of 1, 2 or 3;

p is a value of zero or 1;

r is a value of zero or 1;

t is a value of zero or 1;

$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group;

X means —NH— group; and n is a value of zero, 1 or 2;

and the salts and N-oxides thereof.

4. A compound according to claim 1, wherein $R^1$ stands for hydrogen atom or for methyl group;

$R^2$ stands for hydrogen atom or for methyl group;

$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or a 5- or 6-membered heterocyclic ring containing one or two or three nitrogen atoms, or a 5-membered heterocyclic ring containing one nitrogen atom and one oxygen atom or one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a 6-membered heterocyclic ring containing one nitrogen or a group of the general formula (a), wherein $R^6$ and $R^7$ independently stand for a straight or branched $C_{1-4}$ alkyl group, or a group of the general formula (b), wherein $R^8$ and $R^9$ independently stand for straight or branched $C_{1-4}$ alkyl group;

Z means oxygen atom, or —$NR^{12}$— group, where $R^{12}$ stands for hydrogen atom, straight or branched $C_{1-4}$ alkyl group, benzyl group or acetyl group;

W means nitrogen atom;

m is a value of 2;

o is a value of 2;

p is a value of zero or 1;

r is a value of zero or 1;

t is a value of zero;

$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group;

X means —NH— group; and n is a value of zero, 1 or 2;

and the salts and N-oxides thereof.

5. A compound according to claim 1, wherein $R^1$ stands for hydrogen atom or for methyl group;

$R^2$ stands for hydrogen atom or for methyl group;

$R^3$ stands for a phenyl group, or a 6-membered heterocyclic ring containing one nitrogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a), wherein $R^6$ and $R^7$ independently stands for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein $R^8$ and $R^9$ independently stand for straight or branched $C_{1-4}$ alkyl group or $C_{3-6}$ cycloalkyl group;

Z means oxygen atom, sulphur atom, —CHR$^{11}$—group or —NR$^{12}$— group, where $R^{11}$ and $R^{12}$ independently stand for hydrogen atom, straight or branched $C_{1-4}$ alkyl group, $C_{3-6}$ cycloalkyl group, benzyl group, or —CH$_2$—(C$_{1-5}$ straight or branched acyl) group, —CH$_2$—CH$_2$—O—(C$_{1-4}$ straight or branched alkyl) group or $C_{1-5}$ straight or branched acyl group;

W means nitrogen atom or —CH— group;

m is a value of 1, 2 or 3;

o is a value of 1, 2 or 3;

p is a value of zero or 1;

r is a value of zero or 1;

t is a value of zero or 1;

$R^5$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom;

$R^{13}$ stands for cyano group;

X means —NH— group; and n is a value of zero, 1 or 2;

and the salts and N-oxides thereof.

6. A compound according to claim 1, wherein $R^1$ stands for hydrogen atom or for methyl group;

$R^2$ stands for hydrogen atom or for methyl group;

$R^3$ stands for a phenyl- or thienyl-, or furyl group, optionally substituted with one or more, identical or different, straight or branched $C_{1-4}$ alkyl group, straight or branched $C_{1-4}$ alkoxy group, or halogen atom, or a 5- or 6-membered heterocyclic ring containing one or two or three nitrogen atoms, or a 5-membered heterocyclic ring containing one nitrogen atom and one oxygen atom or one nitrogen atom and one sulphur atom, optionally substituted with one or more, identical or different, straight or branched $C_{1-4}$ alkyl group, straight or branched $C_{1-4}$ alkoxy group, or halogen atom;

$R^4$ stands for a phenyl-, benzyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or a 5- or 6-membered heterocyclic ring containing one or two or three or four nitrogen atoms, or one nitrogen atom and one oxygen atom, or one nitrogen atom and one sulphur atom, optionally substituted with one or more, identical or different, straight or branched $C_{1-4}$ alkyl group, straight or branched $C_{1-4}$ alkoxy group, or halogen atom, or a group of the general formula (a), wherein $R^6$ and $R^7$ independently stands for hydrogen atom, $C_{3-6}$ cycloalkyl group, benzyl group, or a straight or branched $C_{1-4}$ alkyl group, optionally substituted with amino group, amino group substituted with one or two identical or different, straight or branched $C_{1-4}$ alkyl group, hydroxyl group, carboxyl group or straight or branched $C_{1-4}$ alkoxy group, or a group of the general formula (b), wherein $R^8$ and $R^9$ independently stand for straight or branched $C_{1-4}$ alkyl group or $C_{3-6}$ cycloalkyl group;

Z means oxygen atom, sulphur atom, —CHR$^{11}$— group or —NR$^{12}$— group, where $R^{11}$ and $R^{12}$ independently stand for hydrogen atom, straight or branched $C_{1-4}$ alkyl group, $C_{3-6}$ cycloalkyl group, benzyl group, or —CH$_2$—(C$_{1-5}$ straight or branched acyl) group, —CH$_2$—CH$_2$—O—(C$_{1-4}$ straight or branched alkyl) group or $C_{1-5}$ straight or branched acyl group;

W means nitrogen atom or —CH— group;

m is a value of 1, 2 or 3;

o is a value of 1, 2 or 3;

p is a value of zero or 1;

r is a value of zero or 1;

t is a value of zero or 1;

$R^5$ stands for a phenyl group, optionally substituted with methoxy group, hydroxyl group, or halogen atom, or a 5- or 6-membered heterocyclic ring containing one nitrogen atom, or one nitrogen atom and one sulphur atom;

51

$R^{13}$ stands for cyano group;
X means —NH— group; and
n is a value of zero, 1 or 2;
and the salts and N-oxides thereof.

7. A compound according to claim 1,
wherein
$R^1$ stands for hydrogen atom or methyl group;
$R^2$ stands for hydrogen atom or methyl group;
$R^3$ stands for a phenyl- or thienyl-, or furyl group, or
    a 5- or 6-membered heterocyclic ring containing one or two or three nitrogen atoms, or a 5-membered heterocyclic ring containing one nitrogen atom and one oxygen atom or one nitrogen atom and one sulphur atom;
$R^4$ stands for a 5- or 6-membered heterocyclic ring containing one or two or three or four nitrogen atoms, or one nitrogen atom and one oxygen atom, or one nitrogen atom and one sulphur atom, or
    a group of the general formula (a), wherein
        $R^6$ and $R^7$ independently stands for hydrogen atom, $C_{3-6}$ cycloalkyl group, benzyl group, or a straight or branched $C_{1-4}$ alkyl group, or
    a group of the general formula (b), wherein
        $R^8$ and $R^9$ independently stand for straight or branched $C_{1-4}$ alkyl group;
    Z means oxygen atom, or —$NR^{12}$— group, where $R^{12}$ stands for hydrogen atom, straight or branched $C_{1-4}$ alkyl group, $C_{3-6}$ cycloalkyl group, benzyl group, or —$CH_2$—acetyl group, —$CH_2$—$CH_2$—O—$CH_2$—$CH_3$ group or acetyl group;
    W means nitrogen atom or —CH-group;
    m is a value of 2;
    o is a value of 2;
    p is a value of zero or 1;
    r is a value of zero or 1;
    t is a value of zero;
$R^5$ stands for a phenyl-, thienyl-, or furyl group, optionally substituted with methylenedioxy group, or with one or more, identical or different, straight or branched $C_{1-4}$ alkyl group, straight or branched $C_{1-4}$ alkoxy group, hydroxyl group, trifluoromethyl group, cyano group, or halogen atom, or
    a 5- or 6-membered heterocyclic ring containing one or two or three or four nitrogen atoms, or one nitrogen atom and one oxygen atom, or one nitrogen atom and one sulphur atom;
$R^{13}$ stands for cyano group;
X means —NH— group; and
n is a value of 1;
and the salts and N-oxides thereof.

8. A compound according to claim 1,
wherein
$R^1$ stands for hydrogen atom;
$R^2$ stands for hydrogen atom;
$R^3$ stands for a phenyl group, or a 6-membered heterocyclic ring containing one nitrogen atom;
$R^4$ stands for a 6-membered heterocyclic ring containing one nitrogen atom, or
    a group of the general formula (b), wherein
        $R^8$ and $R^9$ stand for methyl group;
    Z means oxygen atom, or —$NR^{12}$— group, where $R^{12}$ stands for hydrogen atom, methyl group, benzyl group or acetyl group;
    W means nitrogen atom;
    m is a value of 2;
    o is a value of 2;
    p is a value of zero or 1;
    r is a value of zero or 1;
    t is a value of zero;

52

$R^5$ stands for a phenyl group, optionally substituted with methoxy group, hydroxyl group, or halogen atom, or
    a 5- or 6-membered heterocyclic ring containing one nitrogen atom, or one nitrogen atom and one sulphur atom;
$R^{13}$ stands for cyano group;
X means —NH— group; and
n is a value of 1;
and the salts and N-oxides thereof.

9. A compound according to claim 1, wherein said compound is:
    2-(3-methoxyphenyl)-7-(morpholin-4-yl)-9-benzylamino-10-cyano-s-triazolo[1,5-a]quinoline,
    2-(4-methoxyphenyl)-7-(morpholin-4-yl)-9-benzylamino-10-cyano-s-triazolo[1,5-a]quinoline,
    2-(4-methoxyphenyl)-7-(2,6-trans-dimethylmorpholin-4-yl)-9-benzylamino-10-cyano-s-triazolo[1,5-a]quinoline,
    2-(pyridin-4-yl)-7-(4-methylpiperazin-1-yl)-9-benzylamino-10-cyano-s-triazolo[1,5-a]quinoline,
    2-(4-methoxyphenyl)-7-(4-methylpiperazin-1-yl)-9-benzylamino-10-cyano-s-triazolo[1,5-a]quinoline,
    2-(3-methoxyphenyl)-7-(4-methylpiperazin-1-yl)-9-benzylamino-10-cyano-s-triazolo[1,5-a]quinoline,
    2-(3-hydroxyphenyl)-7-(4-methylpiperazin-1-yl)-9-benzylamino-10-cyano-s-triazolo[1,5-a]quinoline,
    2-(3-methoxphenyl)-7-(4-acetylpiperazin-1-yl)-9-benzylamino-10-cyano-s-triazolo[1,5-a]quinoline,
    2-(3-metoxifenil )-7-(piperazin-1il)-9-benzilamino-10-ciano-s-triazolo[1,5-a]quinoline,
    2-phenyl-7-(pyridin-3-yl)-9-benzylamino-10-cyano-s-triazolo[1,5-a]quinoline,
    2-phenyl-7-(4-methylpiperazin- 1-yl)-9-(2-pyridylmethylamino)-10-cyano-s-triazolo [1,5-a]quinoline, or
    2-(3-methoxyphenyl)-7-(pyridin-3-yl)-9-(4-pyridylmethylamino)-10-cyano-s-triazolo[1,5-a]quinoline,
or a salt or N-oxide thereof.

10. A compound according to claim 1, wherein said compound is:
    2-(3-methoxyphenyl)-7-(morpholin-4-yl)-9-benzylamino-10-cyano-s-triazolo[1,5-a]quinoline hydrochloride,
    2-(4-methoxyphenyl)-7-(morpholin-4-yl)-9-benzylamino-10-cyano-s-triazolo[1,5-a]quinoline hydrochloride,
    2-(4-methoxyphenyl)-7-(2,6-dimethylmorpholin-4-yl)-9-benzylamino-10-cyano-s-triazolo[1,5-a]quinoline hydrogensulfate,
    2-(pyridin-4-yl)-7-(4-methylpiperazin-1-yl)-9-benzylamino-10-cyano-s-triazolo[1,5-a]quinoline maleate,
    2-(4-methoxyphenyl)-7-(4-methylpiperazin-1-yl)-9-benzylamino-10-cyano-s-triazolo[1,5-a]quinoline-hemifumarate monohydrate,
    2-(3-methoxyphenyl)-7-(4-methylpiperazin-1-yl)-9-benzylamino-10-cyano-s-triazolo[1,5-a]quinoline-hemifumarate hemihydrate,
    2-(3-hydroxyphenyl)-7-(4-methylpiperazin-1-yl)-9-benzylamino-10-cyano-s-triazolo[1,5-a]quinoline hydrochloride,
    2-(3-Methoxyphenyl)-7-(4-acetylpiperazin-1-yl)-9-benzylamino-10-cyano-s-triazolo[1,5-a]quinoline hydrogensulfate,
    2-(3-methoxyphenyl)-7-(piperazin-1-yl)-9-benzylamino-10-cyano-s-triazolo [1,5-a]quinoline maleate,
    2-Phenyl-7-(pyridin-3-yl)-9-benzylamino-10-cyano-s-triazolo [1,5-α]quinoline hydrogensulfate, 2-phenyl-7-(4-methylpiperazin-1-yl)-9-(2-pyridylmethylamino)-10-cyano-s-triazolo [1,5-α]quinoline hydrochloride, or 2-(3-Methoxyphenyl)-7-(pyridin-3-yl)-9-(4-pyridylmethylamino)-10-cyano-s-triazolo[1,5-α]quinoline hydrogensulfate.

11. A pharmaceutical composition comprising one or more compounds according to claim 1, or a salt or N-oxide thereof, and one or more pharmaceutically acceptable excipients.

12. A pharmaceutical composition comprising one or more of the compounds according to claim 9 and one or more pharmaceutically acceptable excipients.

13. A pharmaceutical composition comprising one or more of the compounds according to claim 10 and one or more pharmaceutically acceptable excipients.

14. The pharmaceutical composition according to claim 11, wherein said composition comprises an antiasthmatic, antiischemic, antidepressant, antiarrhythmic, antirheumatic, antiglaucomic, antiinflammatory in inflammatory and irritable bowel diseases, antiCOPD, kidney function protective, tumor preventive, antiparkinson agent, or cognitive function stimulating medicament.

15. A compound according to claim 1, wherein:
X is oxygen;
n is zero; and
R3 is hydrogen.

* * * * *